(12) United States Patent
Bales et al.

(10) Patent No.: US 6,494,881 B1
(45) Date of Patent: Dec. 17, 2002

(54) APPARATUS AND METHOD FOR ELECTRODE-SURGICAL TISSUE REMOVAL HAVING A SELECTIVELY INSULATED ELECTRODE

(75) Inventors: Thomas O. Bales, Coral Gables, FL (US); Michael W. Calhoun, Fort Lauderdale, FL (US); Robert Sixto, Jr., Miami, FL (US); John E. Abele, Concord, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 08/940,665

(22) Filed: Sep. 30, 1997

(51) Int. Cl.[7] ............................................. A61B 18/18

(52) U.S. Cl. ........................... 606/45; 606/41; 606/48; 606/49; 606/50

(58) Field of Search ............................ 606/32, 39, 41, 606/45, 46, 47, 48, 49, 50; 604/22

(56) References Cited

U.S. PATENT DOCUMENTS

| 1,814,791 A | 5/1928 | Ende |
| 1,930,214 A | 10/1933 | Wappler |

(List continued on next page.)

FOREIGN PATENT DOCUMENTS

| DE | 37 07 821 A1 | 3/1987 |
| DE | 37 07 820 C2 | 9/1987 |
| EP | 0 544 392 A1 | 6/1993 |
| FR | 2594322 | 2/1986 |
| GB | 2 213 381 A | 8/1989 |
| WO | WO 93/13719 | 7/1993 |
| WO | WO 95/10981 | 4/1995 |
| WO | WO 96/11638 | 4/1996 |
| WO | WO 96/23449 | 8/1996 |
| WO | WO 97/15238 | 5/1997 |
| WO | WO 97/17027 | 5/1997 |
| WO | WO 97/17028 | 5/1997 |
| WO | WO 97/24993 | 7/1997 |
| WO | WO 97/49346 | 12/1997 |

OTHER PUBLICATIONS

US 5,688,268, 11/1997, Billings (withdrawn)
Products for Electrosurgery Product Brochure, by Microvasive, Boston Scientific Corporation, 2 pages.
DLC–14: Diamonex® Product Brochure, by Diamonex® Performance Products, A Unit of Monsanto Company, 33 pages; 1997.
International Search Report for PCT/US98/20112, 9 pages, Feb. 8, 1999.

(List continued on next page.)

Primary Examiner—Rosiland S. Kearney
(74) Attorney, Agent, or Firm—Testa, Hurwitz & Thibeault, LLP

(57) ABSTRACT

An electro-surgical device for performing tissue resection and cauterization includes an elongated body, a pair of arms extending from a distal end of the elongated body, and an electrode in communication with the pair of arms. The elongated body is adapted to be coupled to a source of energy at a proximal end. The electrode has a first region coated with an insulative coating and a second region for focusing energy emission. The coating can be a diamond-like carbon coating or other coating exhibiting resistance to cracking at high temperatures and high voltages. The coating can be deposited on a base section of a loop electrode while the end sections remain free of the coating. Alternatively, the coating can be unevenly deposited on the electrode. In other embodiments, the electrode can comprise a rollerball and the insulative coating can be deposited on selected or random portions of the rollerball. The insulative coating prevents energy loss to fluid and tissue during the operation, thus allowing resection and cauterization to be efficiently performed.

12 Claims, 23 Drawing Sheets

U.S. PATENT DOCUMENTS

| | | |
|---|---|---|
| 1,963,636 A | 6/1934 | Wappler |
| 2,056,377 A | 10/1936 | Wappler |
| 2,090,923 A | 8/1937 | Wappler |
| 2,101,913 A | 12/1937 | Meyer |
| 2,487,502 A | 11/1949 | Willinsky |
| 3,149,633 A | 9/1964 | Zingale |
| 3,910,279 A | 10/1975 | Okada et al. |
| 3,939,839 A | 2/1976 | Curtiss |
| 3,973,568 A | 8/1976 | Iglesias |
| 3,982,542 A | 9/1976 | Ford et al. |
| 3,985,137 A | 10/1976 | Donohue |
| 4,051,855 A | 10/1977 | Schneiderman |
| 4,060,087 A | 11/1977 | Hiltebrandt et al. |
| 4,103,688 A | 8/1978 | Edwards |
| 4,116,198 A | 9/1978 | Roos |
| 4,134,406 A | 1/1979 | Iglesias |
| 4,149,538 A | 4/1979 | Mrava et al. |
| 4,190,051 A | 2/1980 | Iglesias |
| 4,333,467 A | 6/1982 | Domicone |
| 4,347,849 A | 9/1982 | Congdon |
| 4,538,610 A | 9/1985 | Kubota |
| 4,648,399 A | 3/1987 | Nakada |
| 4,649,917 A | 3/1987 | Karasawa |
| 4,674,499 A | 6/1987 | Pao |
| 4,848,346 A | 7/1989 | Crawford |
| 4,862,890 A | 9/1989 | Stasz et al. |
| 4,917,082 A | 4/1990 | Grossi et al. |
| 4,919,131 A | 4/1990 | Grossi et al. ................. 606/46 |
| 4,934,367 A | 6/1990 | Daglow et al. ............. 439/527 |
| 4,936,301 A | 6/1990 | Rexroth et al. |
| 4,976,711 A | 12/1990 | Parins et al. |
| 4,994,062 A | 2/1991 | Nishigaki et al. |
| 5,007,902 A | 4/1991 | Rydell |
| 5,007,907 A | 4/1991 | Nishigaki et al. |
| 5,013,312 A | 5/1991 | Parins et al. ................. 606/37 |
| 5,019,076 A | 5/1991 | Yamanashi et al. ........... 606/45 |
| 5,029,573 A | 7/1991 | Chow |
| 5,041,111 A | 8/1991 | Bauer et al. |
| 5,047,027 A | 9/1991 | Rydell ......................... 606/48 |
| D320,446 S | 10/1991 | Grossi et al. |
| 5,064,424 A | 11/1991 | Bitrolf ......................... 606/46 |
| 5,078,717 A | 1/1992 | Parins et al. ................. 606/48 |
| 5,080,660 A | 1/1992 | Buelna ........................ 606/45 |
| 5,085,658 A | 2/1992 | Meyer ......................... 606/46 |
| 5,088,998 A | 2/1992 | Sakashita et al. |
| 5,098,431 A | 3/1992 | Rydell |
| 5,100,402 A | 3/1992 | Fan |
| 5,122,138 A | 6/1992 | Manwaring |
| 5,125,928 A | 6/1992 | Parins et al. ................. 606/48 |
| 5,171,311 A | 12/1992 | Rydell et al. |
| 5,192,280 A | 3/1993 | Parins |
| 5,196,011 A | 3/1993 | Korth et al. ................. 606/46 |
| 5,197,964 A | 3/1993 | Parins ......................... 606/48 |
| 5,252,090 A | 10/1993 | Giurtino et al. ............ 439/441 |
| 5,258,006 A | 11/1993 | Rydell et al. ............... 606/205 |
| 5,269,780 A | 12/1993 | Roos ........................... 606/42 |
| 5,277,696 A | 1/1994 | Hagen ......................... 606/49 |
| 5,290,286 A | 3/1994 | Parins ......................... 606/50 |
| 5,318,564 A | 6/1994 | Eggers |
| 5,330,470 A | 7/1994 | Hagen |
| 5,366,443 A | 11/1994 | Eggers et al. |
| 5,380,320 A | 1/1995 | Morris |
| 5,395,363 A | 3/1995 | Billings et al. |
| 5,396,900 A | 3/1995 | Slater et al. |
| 5,403,311 A | 4/1995 | Abele et al. .................. 606/49 |
| 5,405,373 A * | 4/1995 | Peterson et al. ............ 607/121 |
| 5,423,812 A | 6/1995 | Ellman et al. |
| 5,451,224 A | 9/1995 | Goble et al. .................. 606/48 |
| 5,484,435 A | 1/1996 | Fleenor et al. ................ 606/46 |
| 5,506,038 A | 4/1996 | Knapp et al. ................ 428/216 |
| 5,508,368 A | 4/1996 | Knapp et al. ................ 427/534 |
| 5,527,331 A | 6/1996 | Kresch et al. ............... 606/170 |
| 5,540,685 A | 7/1996 | Parins et al. |
| 5,569,244 A * | 10/1996 | Hahnen ....................... 606/46 |
| 5,574,130 A | 11/1996 | Haeussling et al. ......... 528/354 |
| 5,593,406 A | 1/1997 | Eggers et al. |
| D385,351 S | 10/1997 | Manzie et al. |
| 5,681,282 A | 10/1997 | Eggers et al. |
| 5,683,366 A | 11/1997 | Eggers et al. |
| 5,683,443 A | 11/1997 | Munshi et al. |
| 5,693,052 A | 12/1997 | Weaver |
| 5,697,281 A | 12/1997 | Eggers et al. |
| 5,697,536 A | 12/1997 | Eggers et al. |
| 5,697,882 A | 12/1997 | Eggers et al. |
| 5,697,900 A | 12/1997 | Eggers et al. |
| 5,697,926 A | 12/1997 | Weaver |
| 5,709,680 A | 1/1998 | Yates et al. |
| 5,718,709 A | 2/1998 | Considine et al. |
| 5,720,745 A | 2/1998 | Farin et al. |
| 5,746,746 A * | 5/1998 | Garito et al. ................. 606/45 |
| 5,755,717 A | 5/1998 | Yates et al. |
| 5,766,170 A | 6/1998 | Eggers |
| 5,766,171 A | 6/1998 | Silvestrini |
| 5,776,128 A | 7/1998 | Eggers |
| 5,779,701 A | 7/1998 | McBrayer et al. |
| H1745 H | 8/1998 | Paraschac |
| 5,810,764 A | 9/1998 | Eggers et al. |
| 5,810,808 A | 9/1998 | Eggers |
| 5,810,811 A | 9/1998 | Yates et al. |
| 5,827,274 A | 10/1998 | Bonnet et al. |
| 5,830,214 A | 11/1998 | Flom et al. |
| 5,833,689 A * | 11/1998 | Long ........................... 606/48 |
| 5,843,019 A * | 12/1998 | Eggers et al. ................. 604/22 |
| 5,846,241 A | 12/1998 | Kittur et al. |
| 5,860,976 A | 1/1999 | Billings et al. |
| 5,871,469 A | 2/1999 | Eggers et al. |
| 5,888,198 A | 3/1999 | Eggers et al. |
| 5,919,191 A | 7/1999 | Lennox et al. |
| 6,033,400 A | 3/2000 | Grossi et al. |

OTHER PUBLICATIONS

American ACMI, "ACMI Adult Resectoscopes Operating & Maintenance Manual", Jun. 1984.

The Gray Sheet, "Arthrocare Urological, Gynecological Electrosurgery Systems Under Review by FDA, Firm says in IPO Filing: Launch of Core Arthroscopic Systems Begins", FDC Acc. No. 01220040006, vol. 22, Iss. 4, Jan. 22, 1996.

* cited by examiner

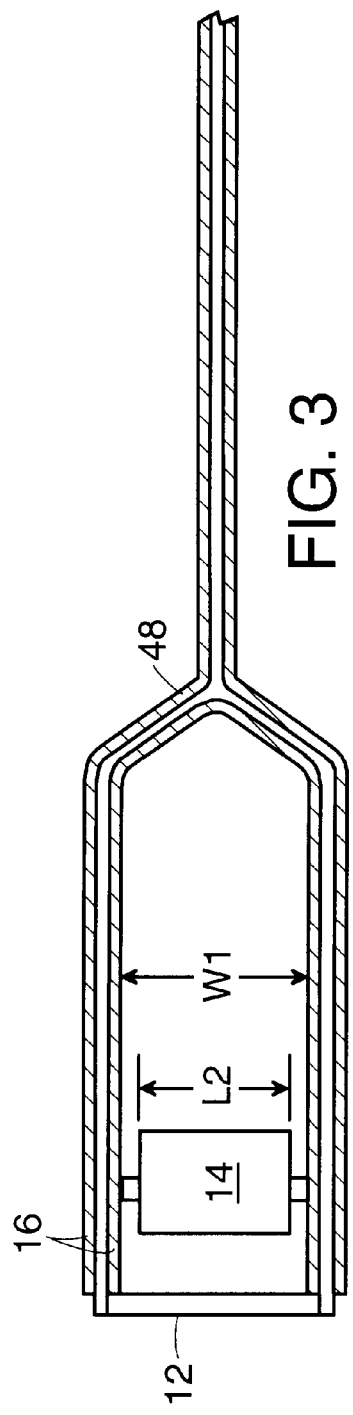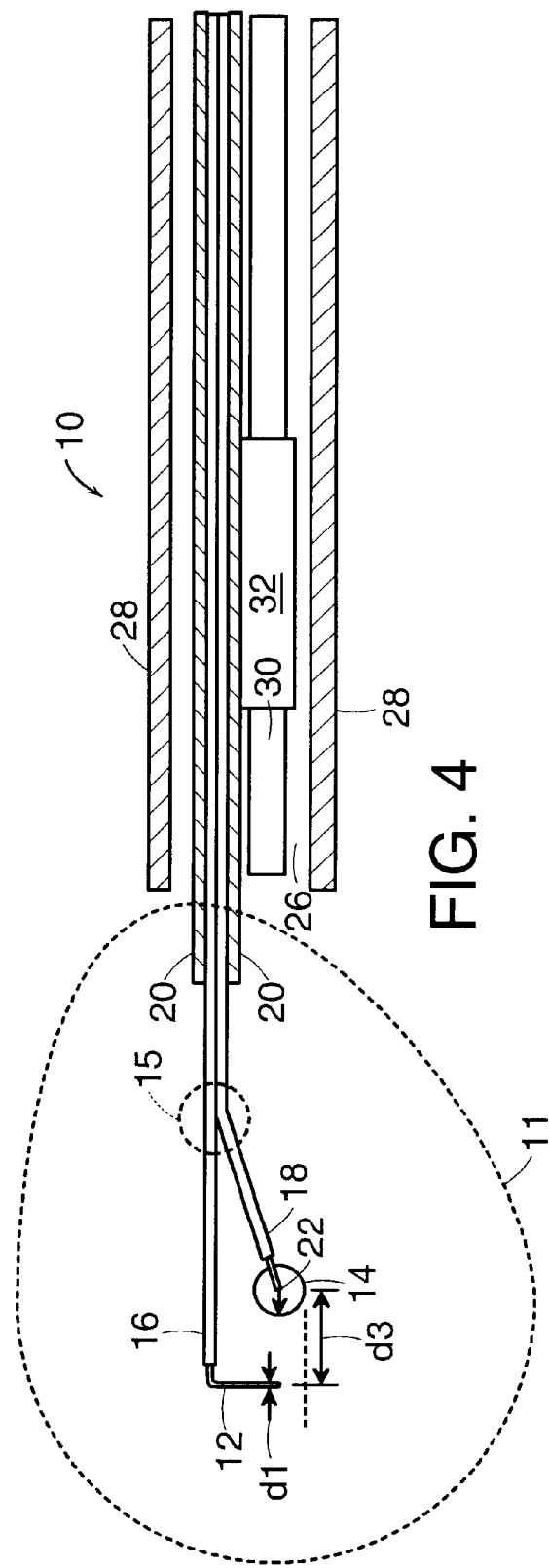

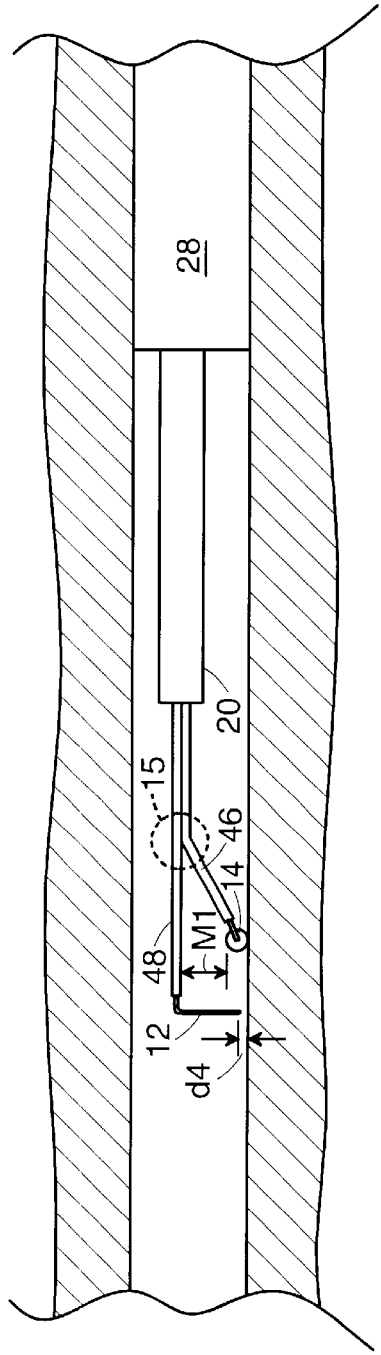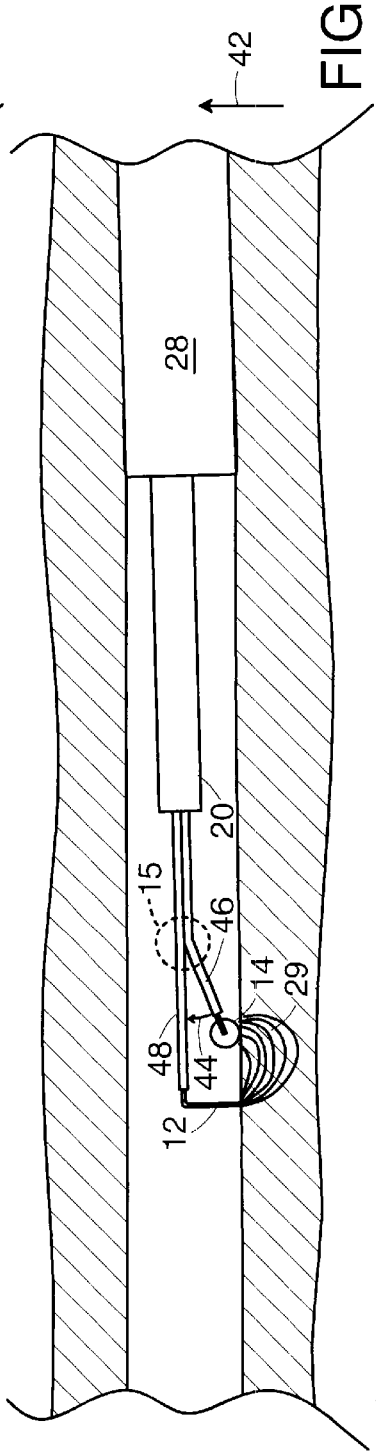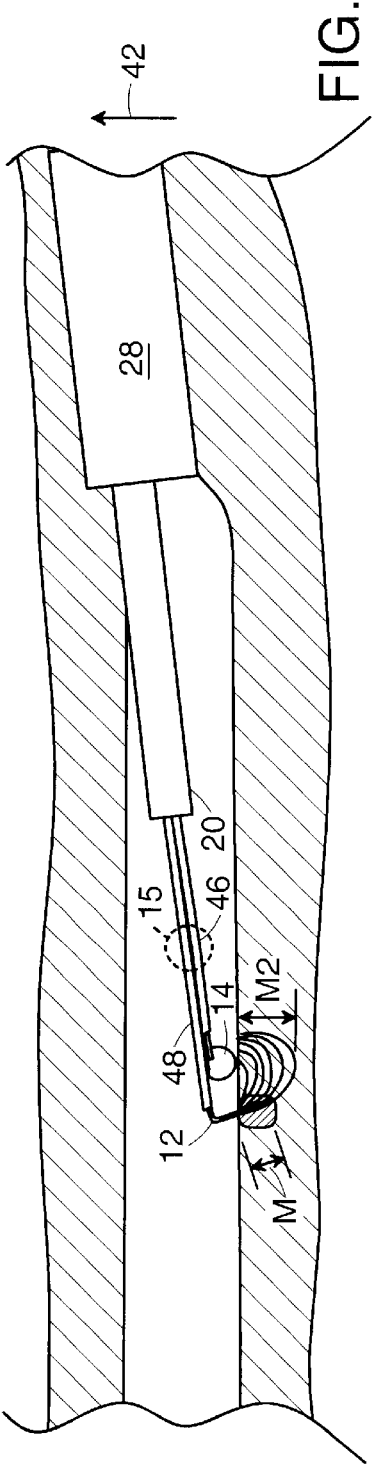

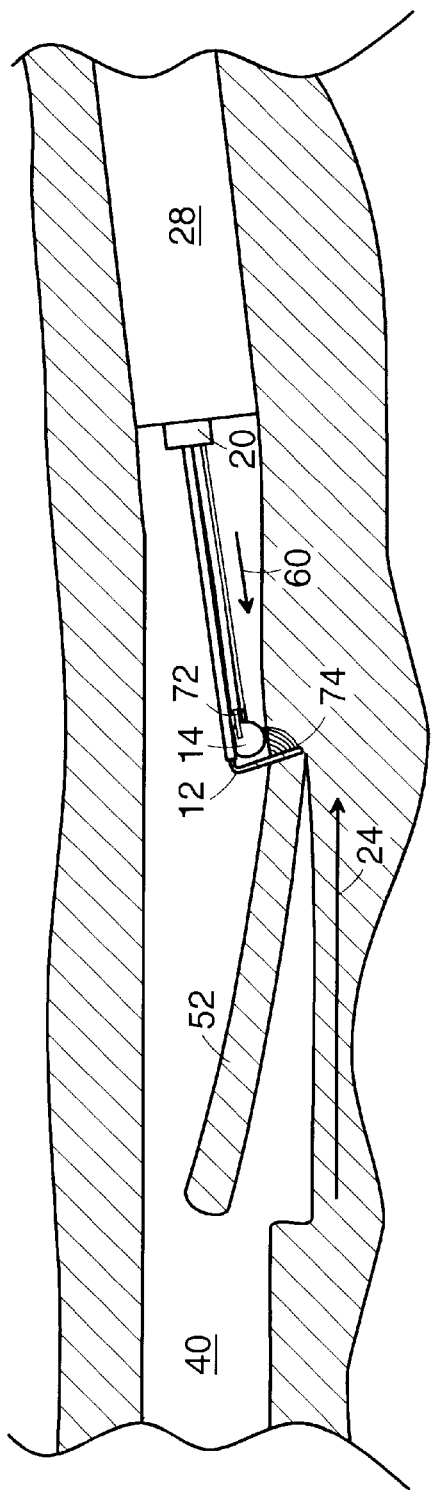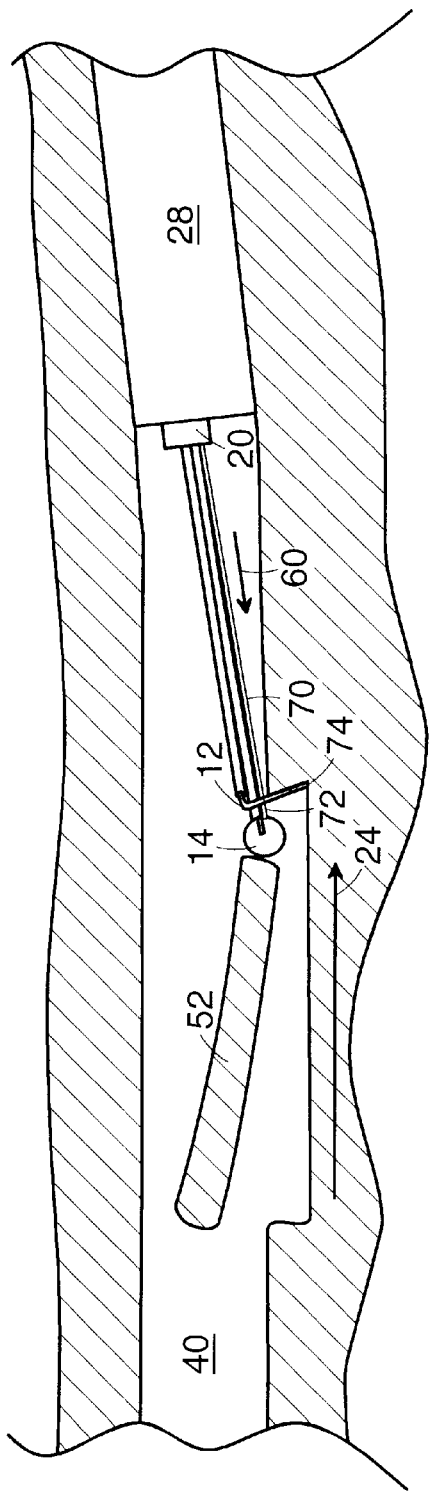

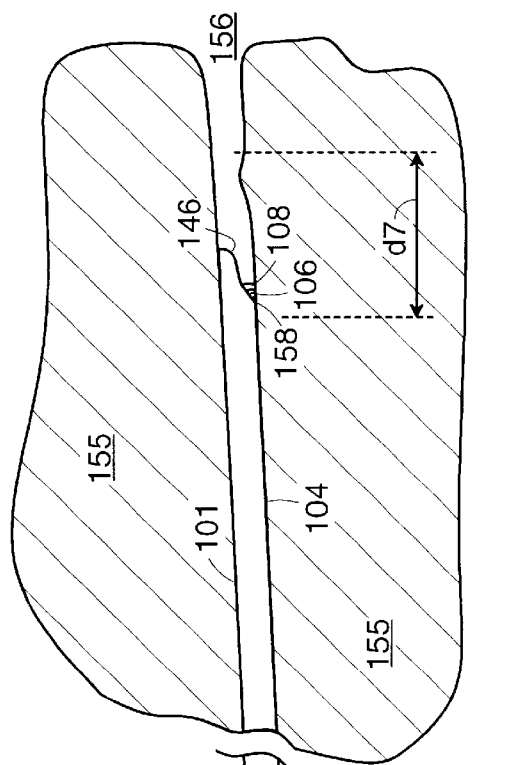
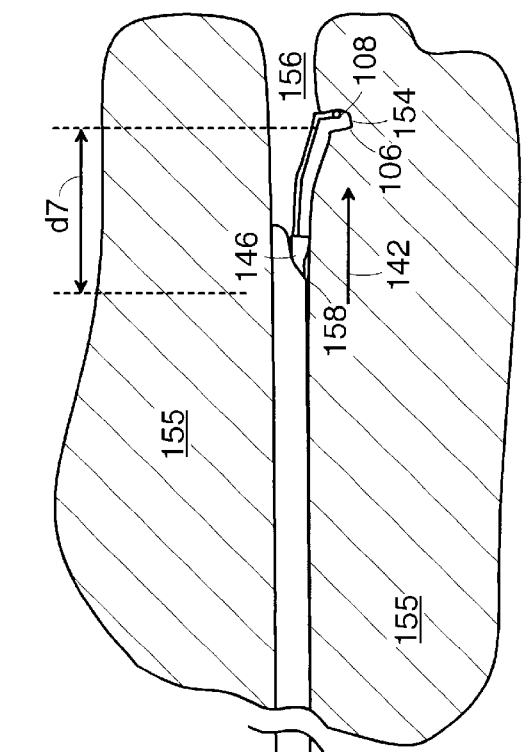
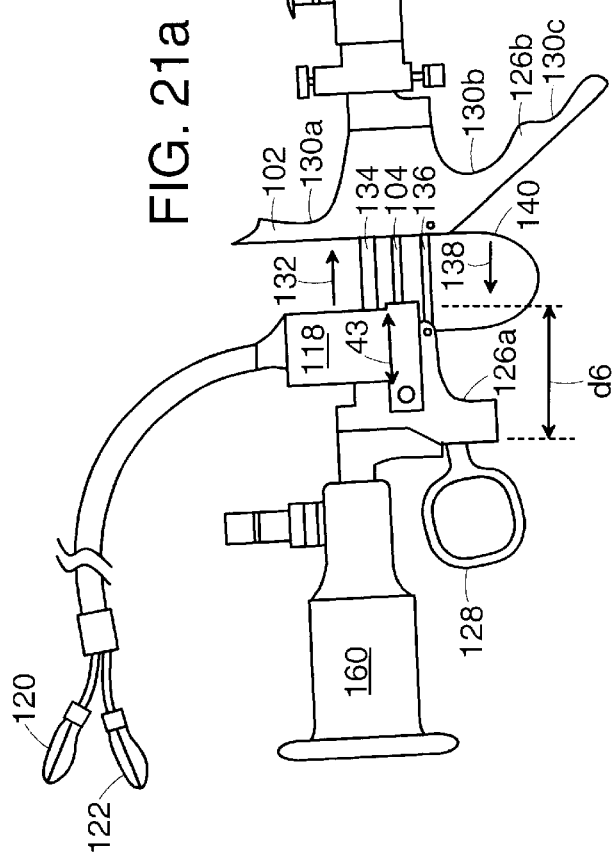
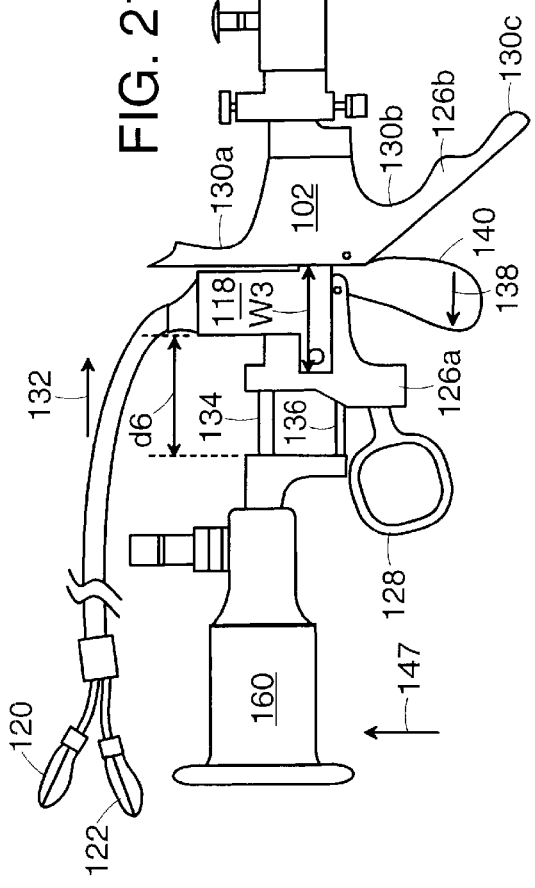
FIG. 21a  FIG. 21b

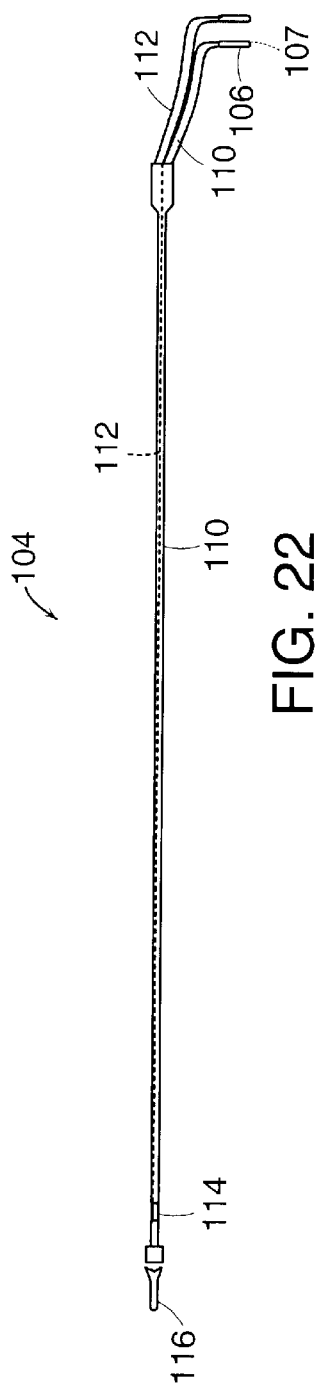
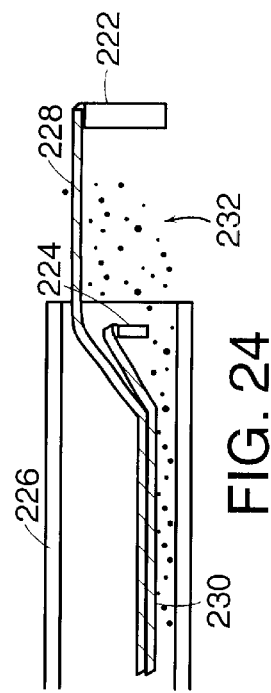
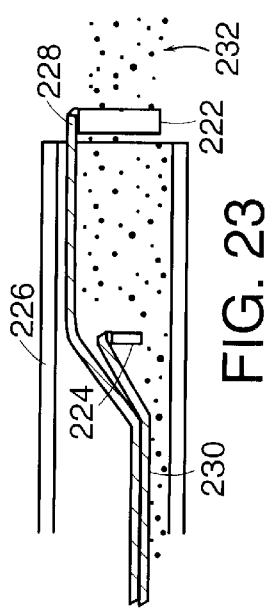
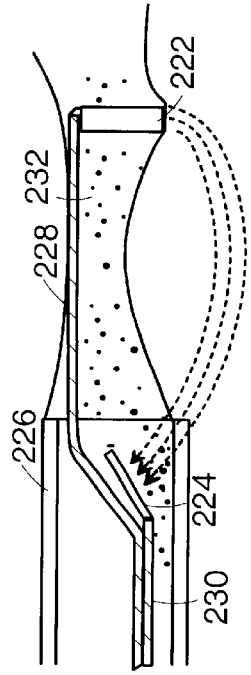
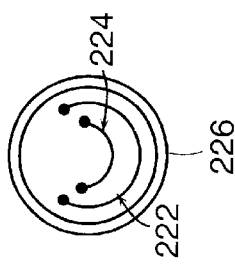

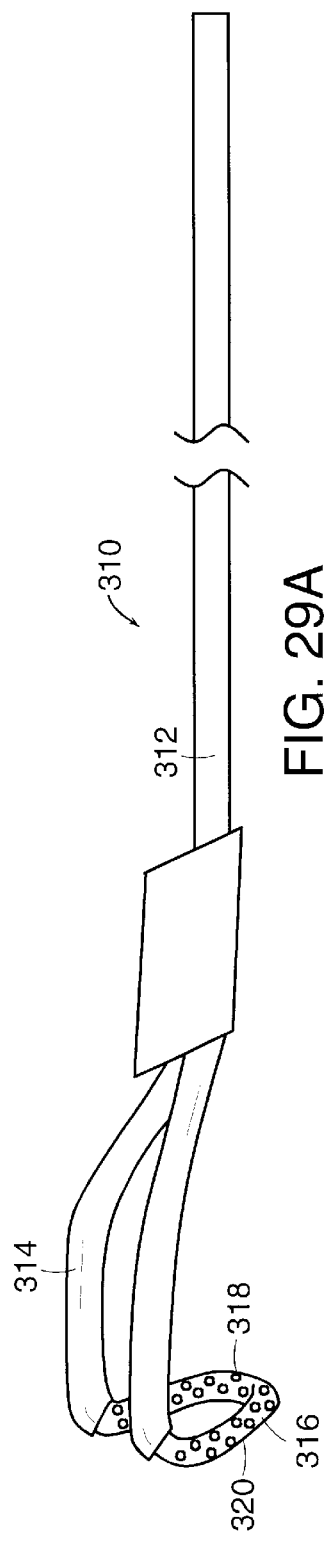
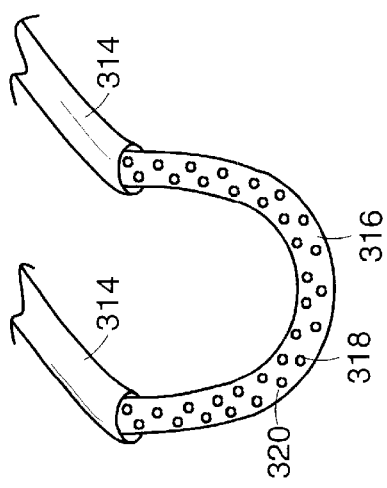
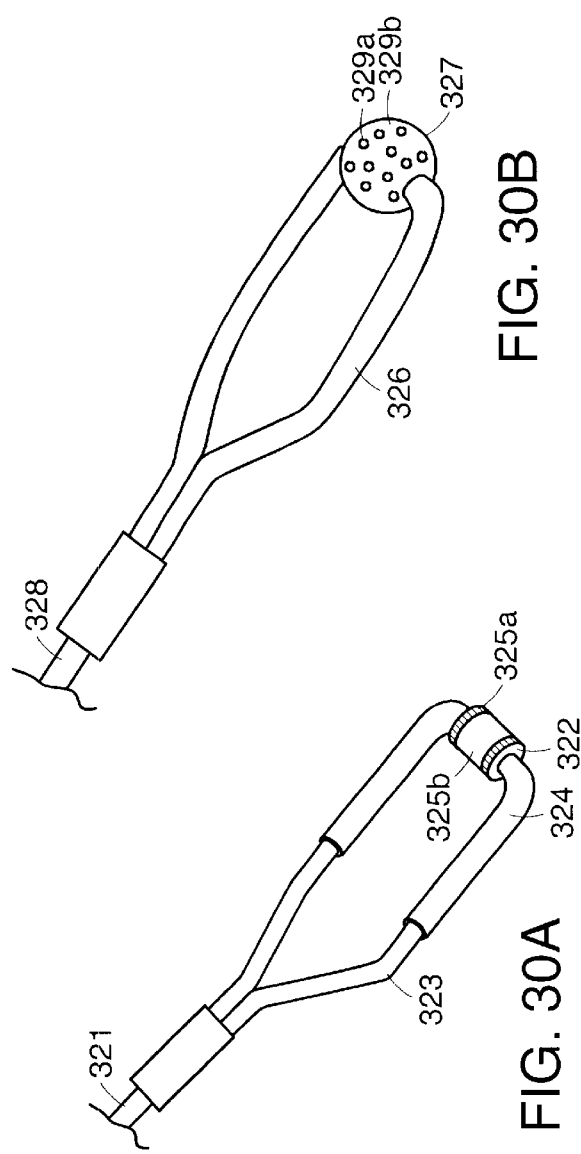
FIG. 29A
FIG. 29B
FIG. 30A
FIG. 30B

APPARATUS AND METHOD FOR ELECTRODE-SURGICAL TISSUE REMOVAL HAVING A SELECTIVELY INSULATED ELECTRODE

FIELD OF THE INVENTION

This invention relates to electro-surgical devices, and more particularly to improved electro-surgical devices having selectively insulated portions for use in resection and cauterization procedures.

BACKGROUND

There are many medical procedures in which tissue is cut or carved away for diagnostic or therapeutic reasons. For example, a transurethral resectioning of the prostate (TURP) is performed to treat benign or cancerous prostatic hyperplasia. Transurethral resectioning may also be performed in the bladder (TURB). The obstructing tissue can be resected, ablated, or coagulated with any number of electro-cautery devices which are inserted into the urethra through a resectroscope. An electric current heats the tissue sufficiently to break inter-cellular bonds, cutting the tissue, or denaturing the tissue in order to remove or perform coagulation on tissue.

Extensive bleeding can occur as a result of electro-resectioning, which can obstruct the physician's view and lead to dangerous blood loss levels. Additionally, during these procedures a pressure differential exists between the urinary tract and the circulatory system. This pressure differential may result in an uptake of ambient fluid during the procedure, possibly causing complications. The bleeding can be treated or avoided by coagulating the tissue in the treatment area with an electro-coagulator that applies a low level current to denature cells to a sufficient depth without breaking intercellular bonds.

Existing electro-cautery devices tend to be inefficient when used with an electrolytic fluid such as saline, because energy applied to a resecting electrode rapidly diffuses into the fluid and chips that have already been removed, due to the conductive nature of the fluid and tissue. As a result, resection is either inadequately carried out, or a greater amount of energy is applied to the electrode to perform resectioning, raising a concern that adjacent healthy tissues may be damaged during the resectionig procedure.

It is therefore an object of the invention to provide an electrosurgical probe that can adequately perform electro-cautery while focusing the energy on the desired location.

SUMMARY OF THE INVENTION

The present invention features an electrosurgical device that is made more efficient and safer than conventional electrosurgical probes by selectively coating portions of the electrode in the device with an insulative or dielectric coating. The present invention provides an appropriate insulative coating that is capable of remaining adhered to an electrode during a resectioning procedure, in which the electrode is subjected to extremely high temperatures and voltages. Various polymer materials including Teflon, and ceramic materials have been tried as insulative coatings, however, such materials have been known to crack under a high temperature environment and therefore are unsuitable as coating materials for resecting electrodes.

In one aspect, the invention features an electro-surgical device, having an elongated body, a pair of arms extending from a distal end of the elongated body, and a loop electrode connecting the pair of arms. The elongated body is adapted to be coupled to a source of energy at a proximal end. The loop electrode defines a pair of end sections and a base section, and is formed of a conductive material. Each end section is coupled to an aim and comprises the conductive material having an insulative coating disposed thereon. The base section disposed between the end sections comprises the conductive material free of the insulative coating, thereby focusing energy emission to the tissue undergoing resection and cauterization.

In one embodiment, the insulative coating on the end sections can be a diamond-like coating or other coating having sufficient properties permitting it to withstand high voltages and temperatures. In another embodiment, the diamond-like coating can be vapor deposited onto the end sections. The insulative coating can have a thickness up to about 10 microns.

In another embodiment, the electro-surgical device comprises an elongated body, a pair of arms extending from a distal end of the elongated body, and an electrode in communication with the pair of arms. The elongated body is adapted to be coupled to a source of energy at a proximal end. The electrode has a first region covered with an insulative coating and a second region covered with a sacrificial material. The sacrificial material covering the second region disintegrates during the application of normal energy levels, exposing a conductive region underneath.

In another embodiment, the insulative coating can be vapor deposited on the first region, and the sacrificial material can be deposited on the second region by dipping, spraying, or brushing. The insulative coating is capable of remaining adhered to the first region upon application of a voltage of up to from about 1000 volts to about 2000 volts (rms) at mains frequency. The insulative coating can be a diamond-like coating.

In still another embodiment, the electro-surgical device comprises an elongated body, a pair of arms extending from a distal end of the elongated body, and an electrode in communication with the pair of arms. The elongated body is adapted to be coupled to a source of energy at a proximal end. The electrode has a non-uniformly deposited insulative coating capable of remaining adhered to the electrode upon application of a voltage of up to about 200 volts (rms), wherein the areas where the coating is thinner can degrade exposing the portion of the electrode which comprises the second region, focusing energy emission.

In another embodiment, the insulative coating can have a hardness of greater than 1000 kg/mm$^2$, a dielectric strength of greater than about 100 volts (rms) per $\mu$m and an electrical resistivity in the range from 10$^2$ ohm-cm to 10$^2$ ohm-cm. In yet another embodiment, the electrode can be a cylindrical roller electrode, or a spherical roller electrode.

In another aspect, the invention features a resectoscope assembly. The assembly includes a resectoscope having a channel and an electro-surgical device insertable through the channel. The electro-surgical device includes an elongated body, a pair of arms in communication with the elongated body and a distal electrode in communication with the pair of arms. The electrode has a first region coated with an insulative coating and a second region for focusing energy emission. The insulative coating is capable of remaining adhered to the electrode upon application of a voltage of up to 500 volts (rms) at mains frequency.

In still another aspect, the invention features a method for performing selective cauterization. An electro-surgical device is positioned along a treatment path near tissue to be resected. The electro-surgical device includes an elongated body, a pair of arms in communication with the elongated body and a distal electrode in communication with the pair of arms. The electrode has a first region coated with an insulative coating and a second region for focusing energy emission. The insulative coating is capable of remaining adhered to the electrode upon application of a voltage of up to 500 volts (rms) at mains frequency. The tissue is flushed with a non-osmotic fluid. A plasma field is generated near the second region of the electrode and the tissue. The electro-surgical device is moved along the treatment path to resect and coagulate the tissue.

In each of the above embodiments, the electro-surgical device can be efficiently used with a non-osmotic fluid, such as, for example, saline, glycine or sorbitol. Moreover, the electro-surgical device of the present invention can be used in saline, an electrolytic, non-osmotic fluid without a considerable loss of energy to the tissue undergoing treatment or the fluid. Additionally, the present invention avoids the use of high currents to deliver energy to the treatment site, as energy is effectively focused in the conductive section or sections of the electrode. The result is higher current density, which promotes the generation of a plasma field.

The foregoing and other objects, features, and advantages of the invention will become apparent from the following, more particular description of the preferred embodiments of the invention.

BRIEF DESCRIPTION OF THE DRAWINGS

This invention is described with particularity in the appended claims. The above and further advantages of this invention may be better understood by referring to the following description taken in conjunction with the accompanying drawings.

FIG. 1a is a perspective view of an electro-surgical device positioned within a resectoscope.

FIG. 1b is a perspective view of the electro-surgical device of FIG. 1a.

FIG. 2 is an enlarged perspective view of a-distal portion of the electro-surgical device of FIG. 1a.

FIG. 3 is an enlarged top view of the distal portion of the electro-surgical device of FIG. 1.

FIG. 4 is an enlarged cross-sectional side view of the distal portion of the electro-surgical device of FIG. 1a.

FIGS. 5–9 are cross-sectional side views of the distal portion of the electro-surgical device of FIG. 1a in use within a urethra.

FIGS. 10 and 11 are cross-sectional side views illustrating structure and use of another embodiment of an electro-surgical device.

FIGS. 21a–21c are cross-sectional side views of the electro-surgical device of FIG. 12 in use within a urethra.

FIG. 22 is a side view of another electro-surgical device that can be used in conjunction with the resectoscope of FIG. 12.

FIG. 23 is a side view of another electro-surgical device in a retracted position within a distal portion of a resectoscope.

FIG. 24 is a side view of the electro-surgical device of FIG. 23 in an extended position within the distal portion of the resectoscope.

FIG. 25 is a cross-sectional view of the electro-surgical device of FIG. 23 within the distal portion of the resectoscope.

FIG. 26 is a side view of another electro-surgical device in an extended position within the distal end of a resectoscope.

FIG. 27b is an enlarged perspective view of a distal portion of the electro-surgical device of FIG. 27a.

FIG. 29a is a perspective view of another electro-surgical device having a loop electrode.

FIG. 29b is an enlarged perspective view of a distal portion of the electro-surgical device of FIG. 29a.

FIG. 30a is a perspective view of an electro-surgical device having a cylindrical roller electrode.

FIG. 30b is a perspective view of an electro-surgical device having a spherical roller electrode.

FIG. 31b is an enlarged perspective view from a proximal side of a distal portion of the electro-surgical device of FIG. 31a.

—FIG. 33b is an enlarged perspective view of a distal end of the biopsy forcep of FIG. 33a.

DETAILED DESCRIPTION

Figure 1:
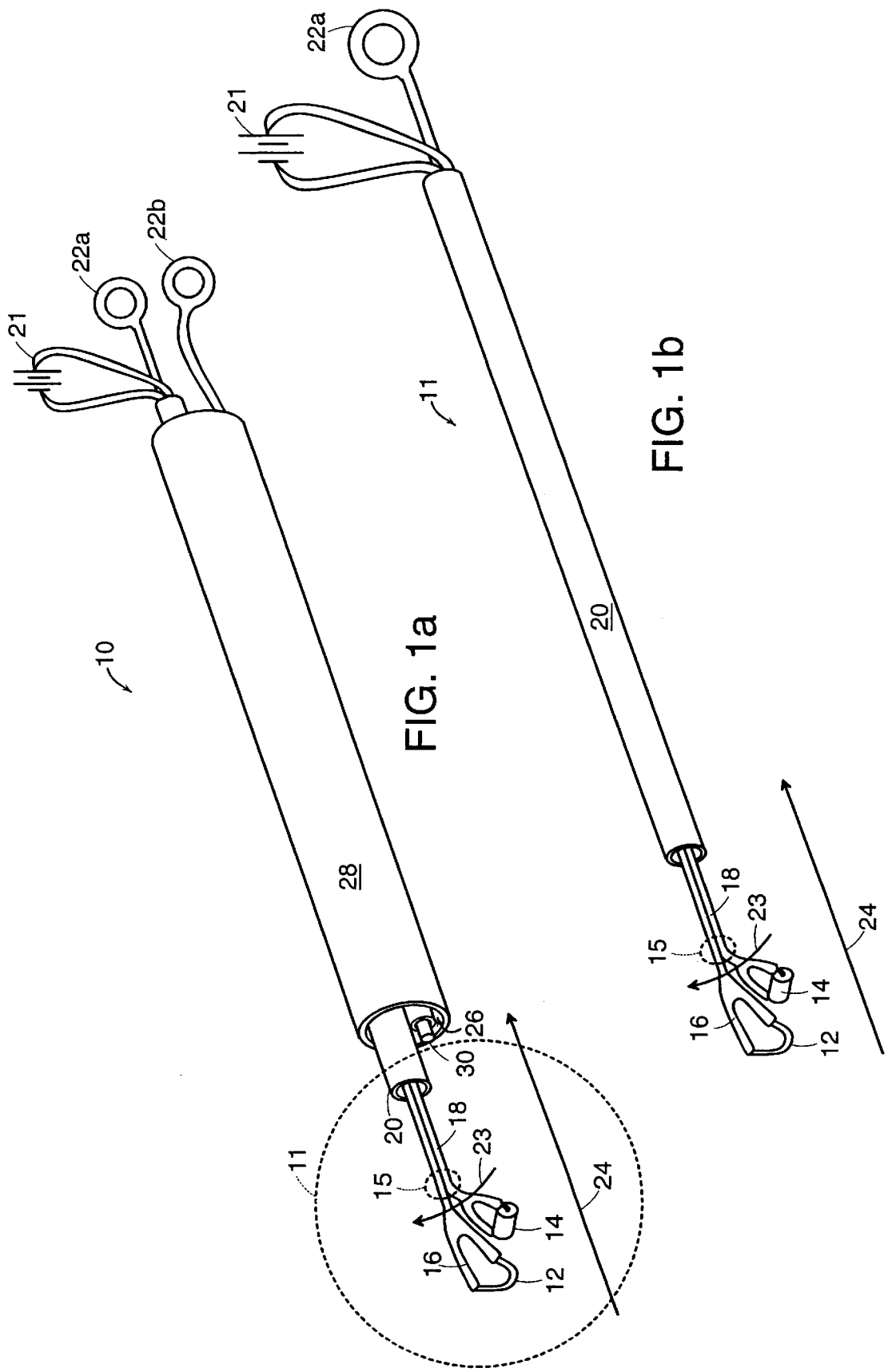

Referring to FIGS. 1a and 1b, shown is one embodiment of a transurethral resection assembly 10 including a resectoscope 28 and a bipolar electro-surgical device 11 having a loop-form resecting electrode 12 and a coagulating electrode 14. When power is applied to the device 11, the larger surface area of coagulating electrode 14 diffuses current to coagulate tissue over a large region while the smaller surface area of resecting electrode 12 concentrates current to resect immediately adjacent tissue. Since the coagulating electrode 14 is positioned ahead of the cutting electrode 12 along a line of resection 24, tissue is coagulated just prior to resection. Coagulating electrode 14 pivots (arrow 23) with respect to resecting electrode 12 through cantilever joint region 15 which controls the depth of resection and coagulation.

Figure 2:
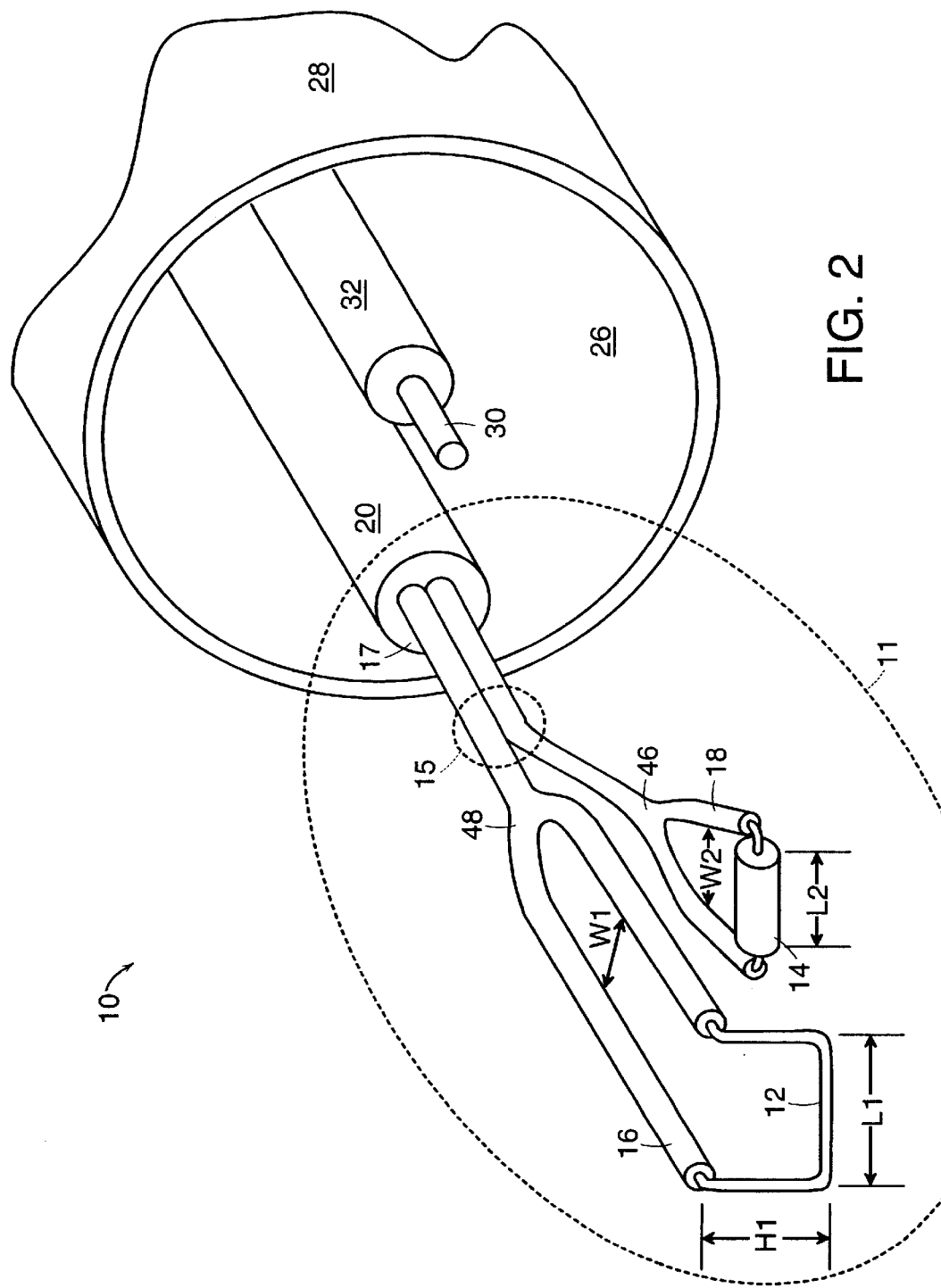

Referring particularly to FIGS. 2 and 3, the width W2 of mounting fork 46 of coagulating electrode 14 and the width W1 of mounting fork 48 of resecting electrode 12 are substantially similar. As a result, mounting fork 48 engages mounting fork 46 to limit the maximum depth of resection to avoid resection of tissue beyond the coagulation zone, as will be described in more detail below.

Resecting electrode 12 and coagulating electrode 14 are connected by wire leads that extend through electrical insulator jackets 16, 18, to a power source 21 (RF generator). The insulated leads extend in close proximity through metal jacket 20 and are axially fixed relative to each other and jacket 20 by epoxy fill 17. Metal jacket 20 terminates proximally in articulation ring 22a as shown in FIGS. 1a and 1b. Ring 22b shown in FIG. 1a is connected to resectoscope 28. Rings 22a and 22b are electrically insulated from the electrodes 12, 14 and enable a physician to move metal jacket 20 and, hence, the electrodes 12, 14 within lumenal space 26 of resectoscope 28 in an axial direction along the resecting path 24.

The resectoscope 28 also includes a telescope 30 that images and illuminates resecting path 24. Telescope 30 is attached to metal jacket 20 through clip 32. As an alternative, separate lumens, one for metal jacket 20 and one for telescope 30, are provided within resectoscope 28. Additionally, lumenal space 26 is used to irrigate and displace fluid, such as urine in the urethra, in the area of resection. Preferably, lumenal space 26 is filled with a non-osmotic, non-electrolytic, high impedance fluid such as glycine (not shown). The non-osmotic nature of glycine reduces damaging cellular fluid absorption, and the non-electrolytic and high impedance nature of glycine insures that the current passed between the electrodes 12, 14 is focused in the tissue between the two electrodes 12, 14.

To reduce the cost of the procedure, distilled water (i.e., deionized water) can be used instead of glycine. Like glycine, distilled water is non-electrolytic. However, unlike glycine, distilled water is osmotic. The substantially bloodless nature of the procedure, however, significantly reduces the amount of fluid absorbed by the patient. Hence, the osmotic nature of distilled water does not typically pose a danger.

In a particular embodiment, resecting electrode 12 is tungsten and coagulating electrode 14 is a silver/copper alloy, and the lead wires (not shown) within insulating jackets 16, 18, respectively, may be made of many materials, including brass, a copper alloy, or a silver alloy.

Resecting electrode 12 has a loopwire diameter d1 of 0.012 inches as shown in FIG. 4, a length L1 of 0.30 inches and a height H of 0.325 inches as shown in FIG. 2. Coagulating electrode 14 is a cylindrical roller with a diameter d2 of about 0.125 to 0.187 inches as shown in FIG. 4 and a length L2 of between 0.187–0.25 inches as shown in FIG. 2. Electrodes 12 and 14 are separated by a distance d3 of approximately 0.187 inches as shown in FIG. 4. Pivoting action of the electrodes 12, 14 can be facilitated by making the mounting fork 48 of resecting electrode 12 stiffer than the mounting fork of coagulating electrode 14, for example, by using a stiffer wire within insulating jacket 18. Metal jacket 20 is made of stainless steel and has an outer diameter of about 0.068 inches, a wall thickness of about 0.005 inches, and an axial length of about 8.0 inches. The power source is a surgical radio frequency (RF) generator, generating a continuous sine wave (i.e., cut waveform) and operating at a typical frequency of 1 MHz and at typical power levels of 100–300 Watts.

Referring to FIGS. 5–9, the operation of electro-surgical device 11 will be described with regard to a transurethral resectioning procedure (TURP). The patient is prepared by inserting a resectoscope 28 to the region of treatment. The physician, with a telescope and irrigation, inspects the region. The region is then flushed with glycine or distilled water.

Referring particularly to FIG. 5, the device 11 is inserted into the patient's urethra 40 through the resectoscope 28 such that resecting electrode 12 and coagulating electrode 14 extend from resectoscope 28. When first inserted, cantilever joint 15 is fully open such that coagulating electrode 14 rests on the surface of tissue to be resected and resecting electrode 12 is suspended a slight distance d4, approximately 0.040 inches, above the surface of the tissue to be resected. The separation is a safety factor since, if power is accidentally applied, current will not pass between the electrodes 12, 14 in a glycine or distilled water environment until both electrodes 12, 14 contact the tissue surface.

Referring to FIG. 6, by applying an upward pressure to the external end of resectoscope 28, as indicated by arrow 42, the physician pivots coagulating electrode 14 with respect to resecting electrode 12, as indicated by arrow 44. This pivoting brings resecting electrode 12 into contact with the tissue to be cut and brings the fork 46 (FIG. 2) of coagulating electrode 14 closer to the fork 48 of resecting electrode 12.

Once both electrodes 12, 14 are in contact with the surface of the tissue to be cut, the physician applies power to the electrodes 12, 14 through hand or foot controls (not shown). As discussed, both electrodes 12 and 14 must contact the tissue because the surrounding glycine or distilled water will not conduct current. Current 50 flows through the tissue between the two electrodes 12, 14. The projected surface area (i.e., shadow or tissue contact area) of coagulating electrode 14 is about 2–5 times larger than the projected surface area of resecting electrode 12. As a result, the current density at resecting electrode 12 is larger than the current density at coagulating electrode 14. The larger surface area of coagulating electrode 14 disburses current over a wide, deep area 29 and causes heating in the area sufficient only to coagulate the tissue (i.e., approximately 60–100° C.). On the other hand, the small surface area of resecting electrode 12 concentrates the current density and causes heating in adjacent tissue sufficient to resect the tissue. Typically, the heating induces a vigorous vaporization in the area immediately adjacent the electrode surface. In some cases, a plasma arc may be generated in the area immediately adjacent the electrode 12 with temperatures of approximately 1000° C. and above. However, lower temperatures, without arcing, can be used for resection.

When the physician increases the upward movement 42 of resectoscope 28, the electrodes 12, 14 pivot bringing electrically insulated forks 46, 48 in contact and causing resecting electrode 12 to resect the tissue to its maximum depth M1 as shown in FIG. 7. Since the length L2, shown in FIG. 3, of coagulating electrode 14 can be less than the width W1 of fork 48, the contact of both insulated forks limits the maximum depth of resection. The maximum depth of resection is limited to prevent resection beyond the depth of coagulation. When forks 46, 48 are in contact, approximately half of coagulating electrode 14 extends between the tines of fork 48. The large surface area and low current density of coagulating electrode 14 keeps coagulating electrode 14 from plunging into the tissue.

Approximately 100–300 Watts of power applied to the electrodes 12, 14 causes resecting electrode 12 to resect to a maximum depth M1 of about 0.20 inches (0.5 cm) and coagulating electrode 14 to coagulate to a maximum depth M2 of about 0.4 inches (1 cm). Coagulating 0.20 inches deeper than resection insures substantially bloodless resection.

Figure 8:
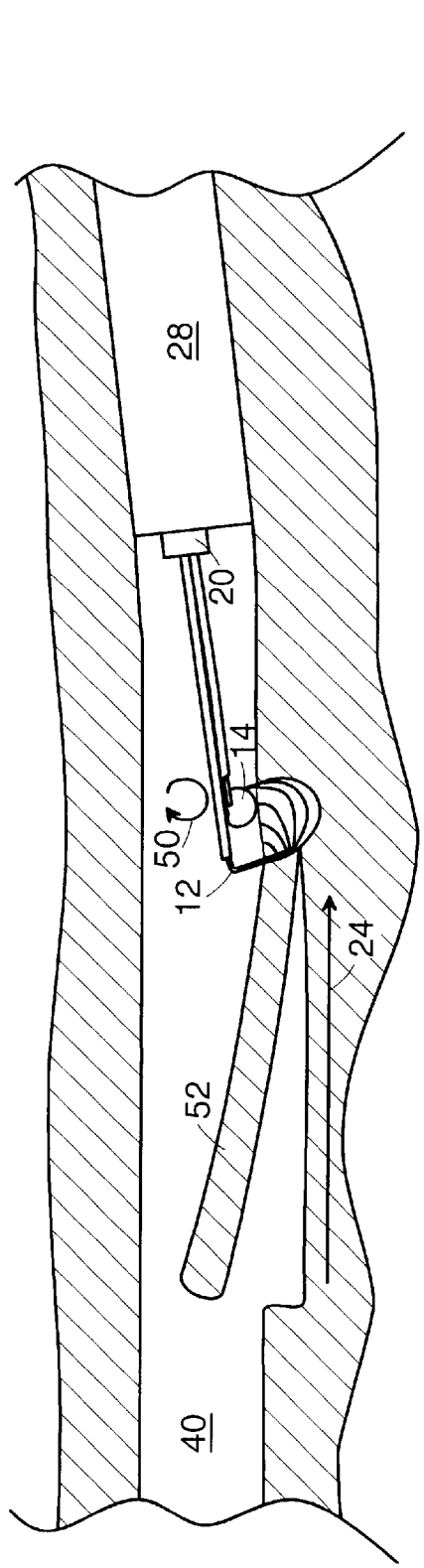
Figure 9:
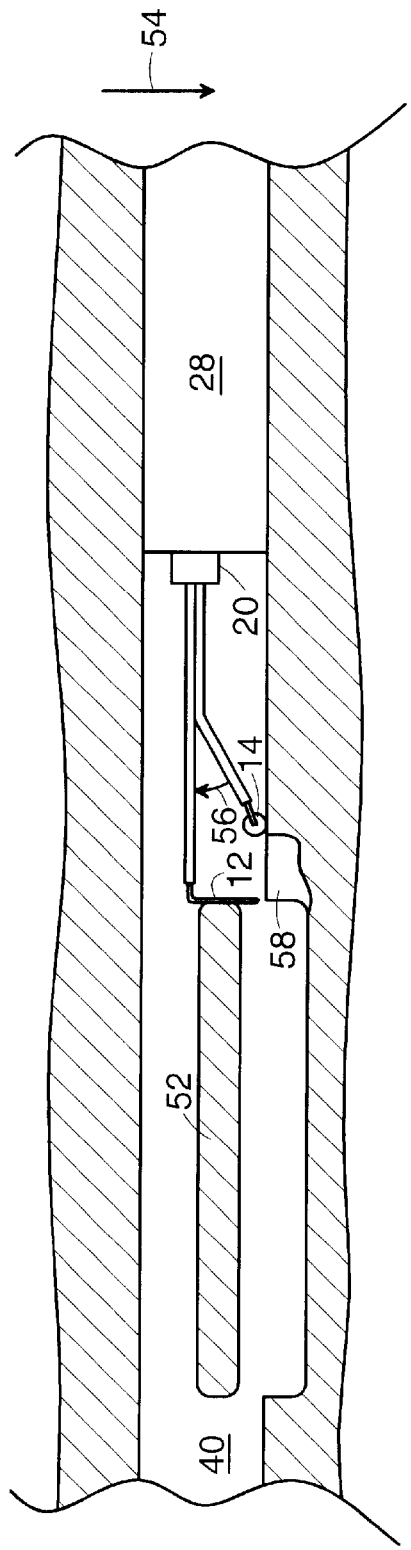

Referring to FIG. 8, the physician squeezes articulation rings 22a and 22b together to pull the device 11 proximally. Coagulating electrode 14 rolls, as indicated by arrow 50, along resecting path 24 and resecting electrode 12 carves a chip 52 of tissue from urethra 40. Referring to FIG. 9, in a typical transurethral procedure, the resecting path is from the bladder to the verumontanum in the prostate (approximately 1.5–10 inches). When the physician has reached the end of resection path 24 such as, for example, the point where the physician wishes to stop resecting, he either stops applying upward pressure to resectoscope 28 allowing urethra 40 to cause resectoscope 28 to move in a downward direction, indicated by arrow 54, or directly applies a downward force to move the resectoscope 28 in the downward direction. This causes cantilever joint 15 to spring open, indicated by arrow 56, pivoting resecting electrode 12 upward and away from coagulating electrode 14. Because coagulating electrode 14 travels ahead of resecting electrode 12 along the resecting path 24, a small portion of coagulated tissue 58 remains in place, that is, the tissue is not resected. During the procedure, the resected chips are normally kept in the patient's bladder, and once the resection is completed, the patient's bladder is evacuated to ensure removal all of the resected chips.

Figure 12:
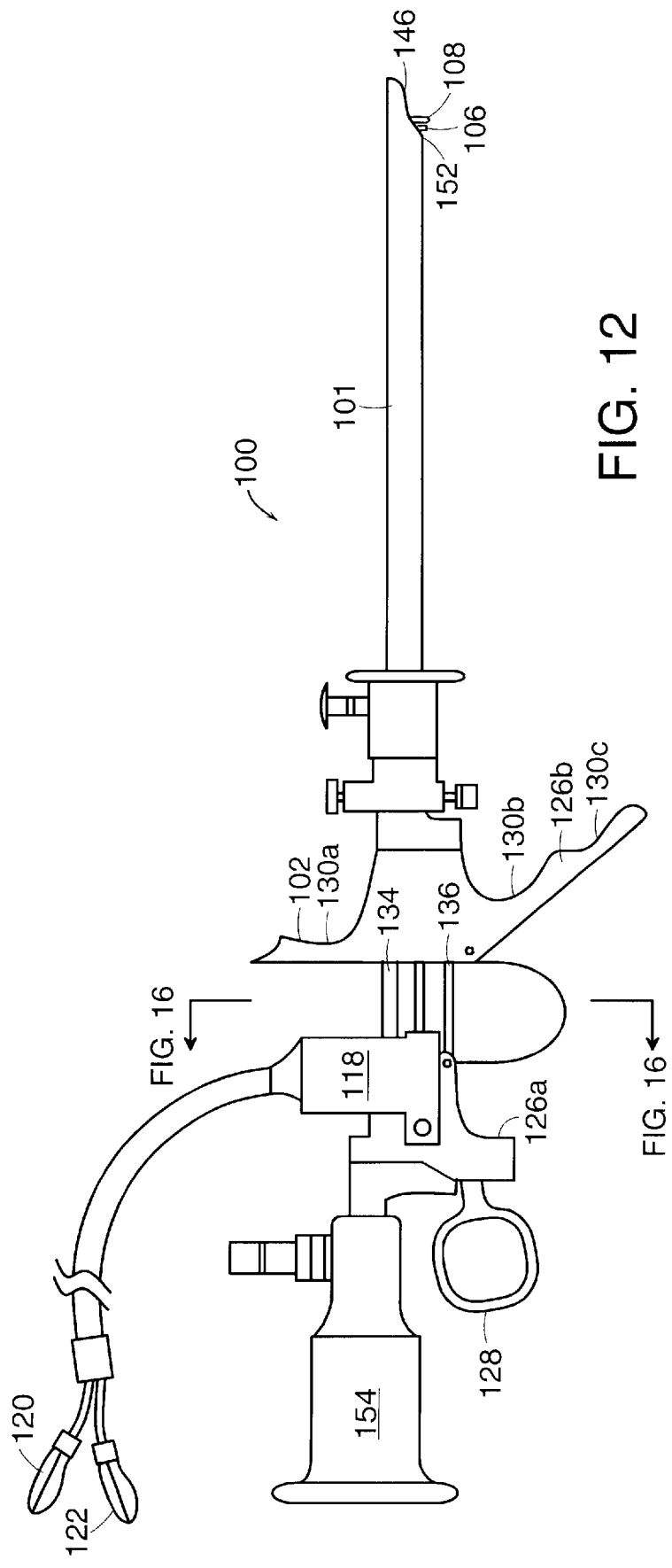
FIG. 12 is a side view of another embodiment of a resectoscope.
Figure 13:
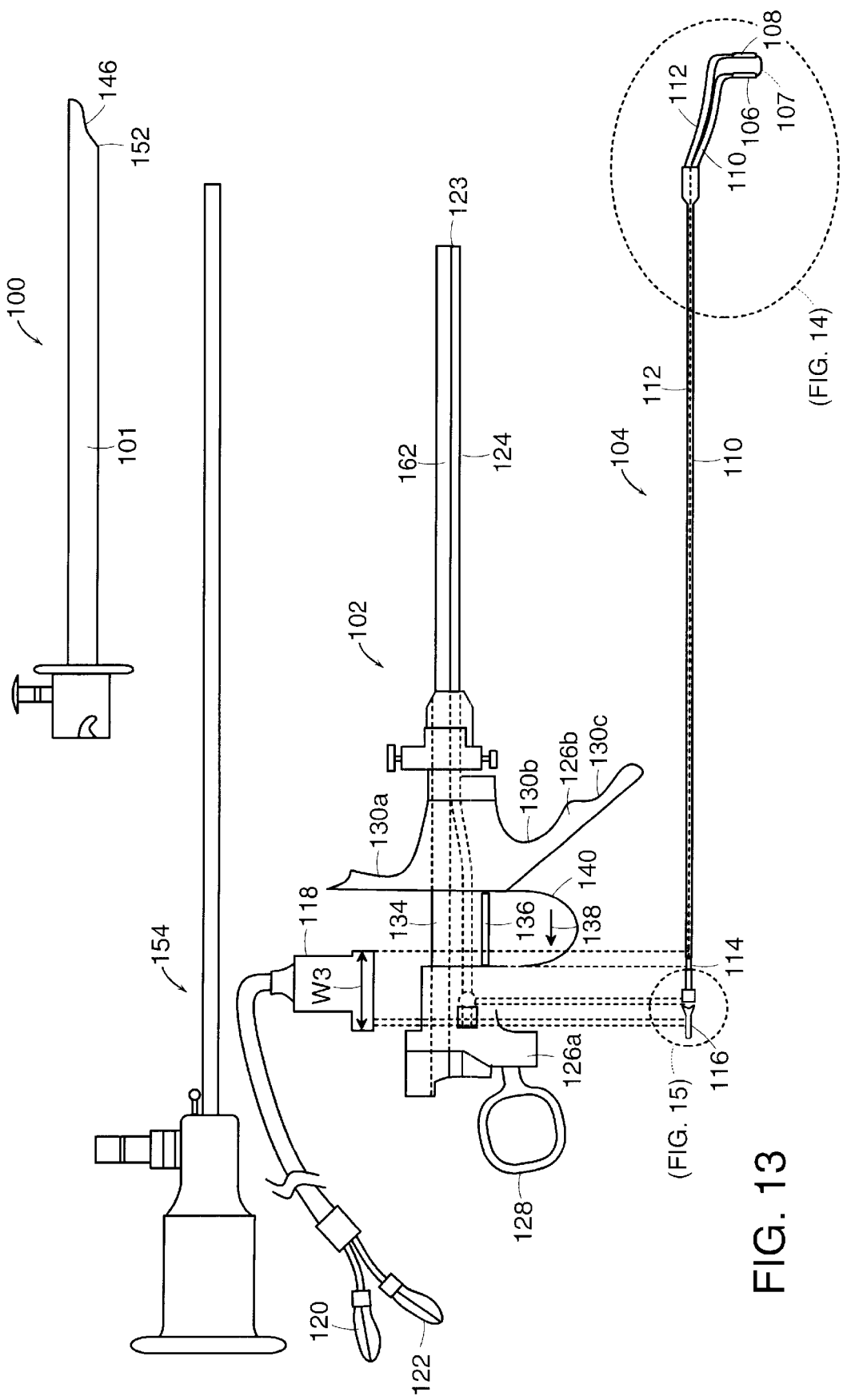
FIG. 13 is an exploded, side view of the resectoscope of FIG. 12.
Figure 14:
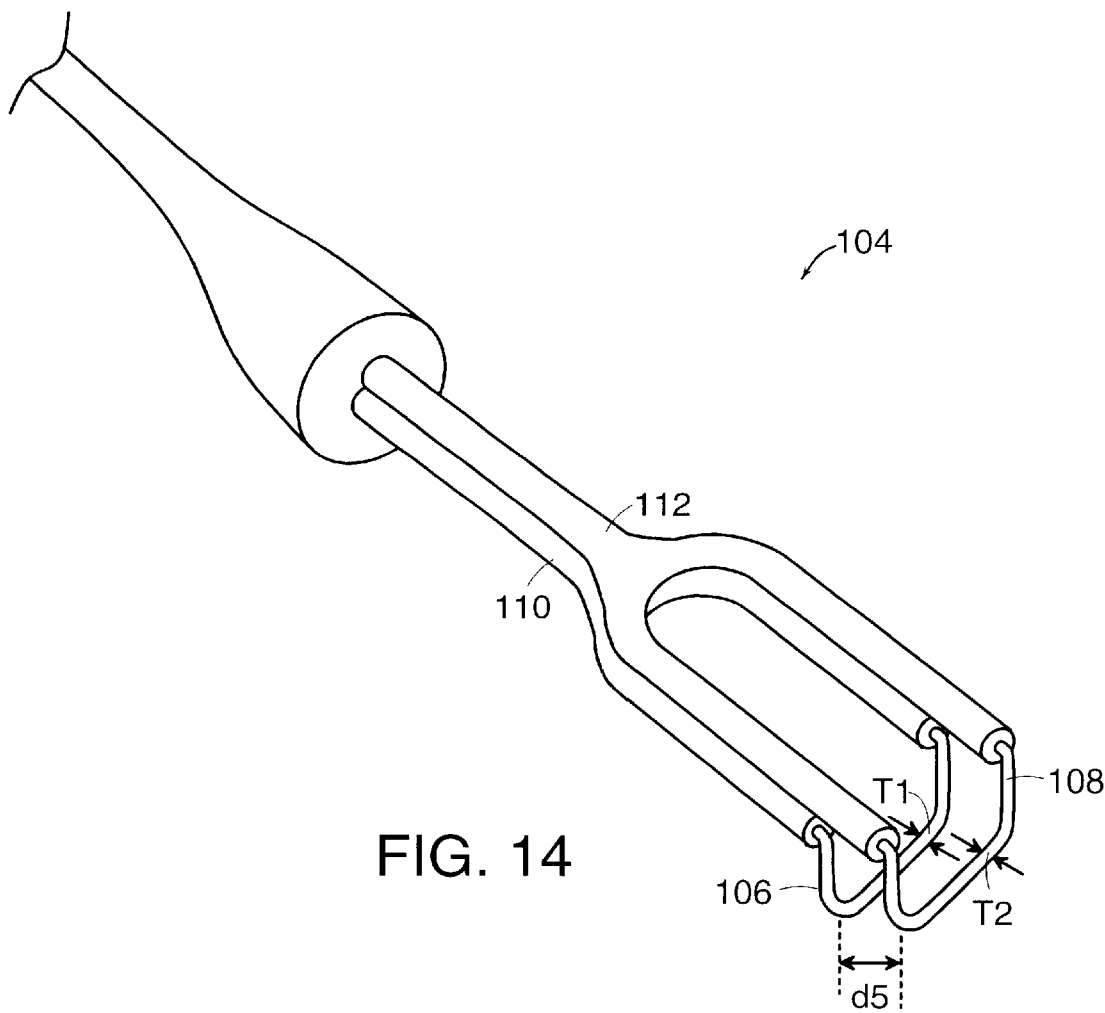
FIG. 14 is an enlarged perspective view of a distal portion of an electro-surgical device used in conjunction with the resectoscope of FIG. 12.

Referring to FIGS. 12–14, another transurethral resection assembly 100 includes an resectoscope, manufactured by Circon ACMI, 102 and a bipolar electro-surgical device 104 having two closely spaced, substantially similar loop-form electrodes 106, 108. The thickness T1, approximately 0.027", of loop electrode 106 is slightly smaller than the thickness T2, approximately 0.030", of loop electrode 108. As a result, loop electrode 106 is the hot or cutting electrode while loop electrode 108 is the cold or return electrode. Loop electrode 106 can be a wedge-shaped electrode of the type described in Hahnen, U.S. Pat. No. 5,569,244, the entire disclosure of which is hereby incorporated herein by reference. When power is applied to the device 104, loop electrode 106 concentrates the current density and causes heating in adjacent tissue sufficient to resect the tissue. The current 107 passing between the electrodes 106, 108 is dispersed over a region of tissue in the area of the incision and causes heating in the region sufficient only to coagulate the tissue in the region. By applying excessive power, approximately 125–300 Watts, to the electrodes 106, 108, the tissue in the area of the incision may be coagulated to a depth sufficient, to minimize or eliminate bleeding.

Spacing two substantially similar loop electrodes a small distance d5, e.g., 0.027", apart provides a low impedance path between the loop electrodes and insures that the current passing between the loop electrodes is confined to a short path. Confining the current path permits safe high power, e.g., 125–300 Watts, electro-surgery. Additionally, the electrodes are capable of resecting tissue in a conductive liquid environment, e.g., saline, because the current is focused in the tissue between the electrodes and is not disbursed through the conductive liquid.

Although coagulating tissue before or substantially simultaneously with tissue resectioning reduces fluid absorption via venous sinus, fluid absorption may still occur. For example, in a myomectomy procedure a tumor is resected from the uterus wall. Prior to tissue resectioning, the uterus is pressure distended with fluid which significantly increases the likelihood of excessive fluid absorption. Excessive absorption of non-ionic fluids such as glycine can lead to life-threatening electrolyte imbalance. Resecting tissue in an ionic liquid environment such as saline reduces the risk of electrolyte imbalance.

Figure 15:
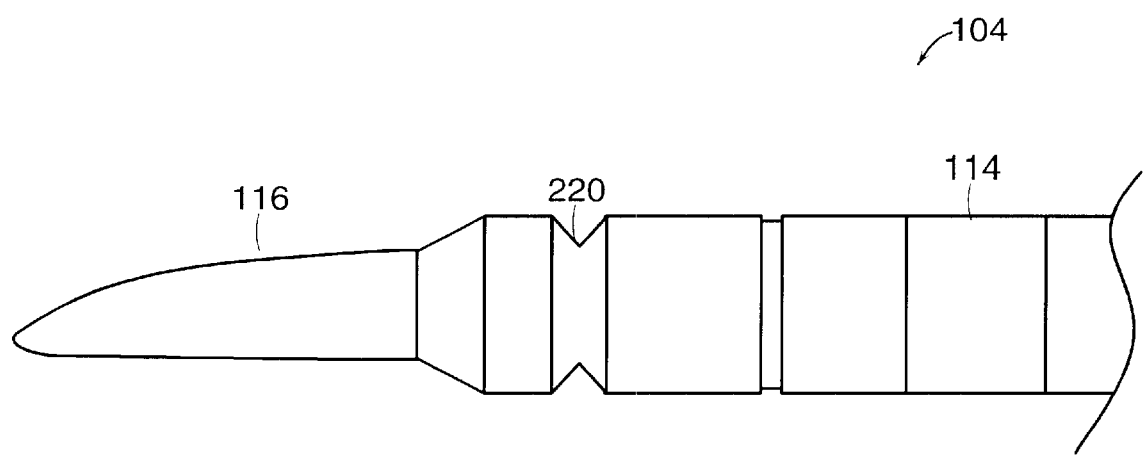
FIG. 15 is an enlarged side view of a proximal portion of the electro-surgical device used lo in conjunction with the resectoscope of FIG. 12.

With reference to FIGS. 13 and 15, loop electrodes 106, 108 are connected by wire leads that extend through electrical insulator jackets 110, 112 to platinum electrical contact ring 114 and brass or bronze electrical contact pin 1 16, respectively, which are mounted on the nylon shaft of bipolar electro-surgical device 104. Pin 116 includes a slot 220 that can be grasped by a knife edge lock in handle portion 126a, as described below. The insulated leads are axially fixed in parallel relative to each other. Bipolar electro-surgical device 104 is inserted into resectoscope 102 through a distal end 123 of a metal jacket 124 in resectoscope 102. A power connector 118 electrically couples ring 114 and pin 116 with banana plugs 120, 122, respectively. During operation, the banana plugs 120, 122 are connected to an RF generator (not shown).

Figure 16:
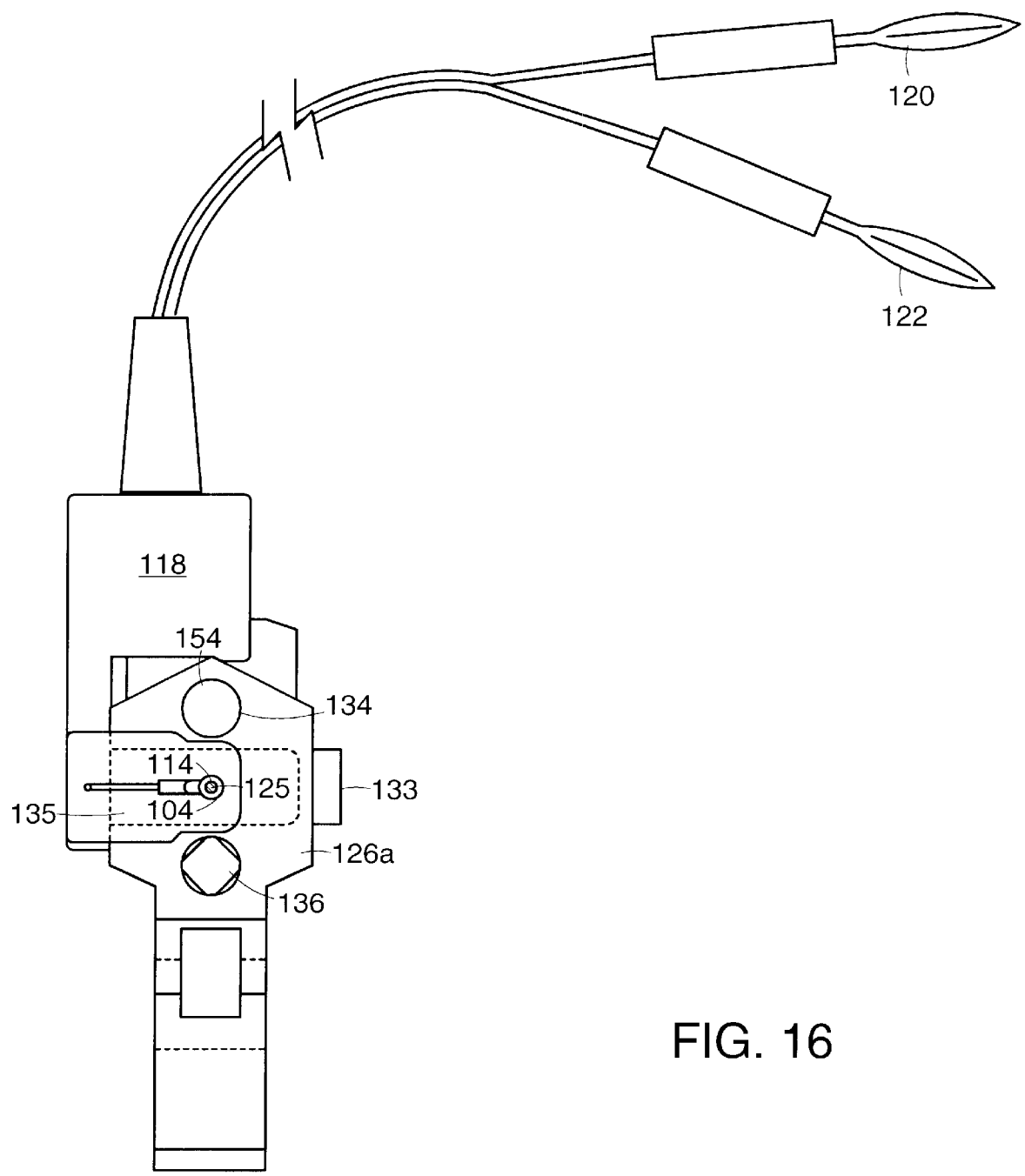
FIG. 16 is an enlarged partially cross-sectional view of a portion of the handle of the resectoscope of FIG. 12 and a bipolar power connector adaptor.

With reference to FIG. 16, power connect 118 is mounted on handle portion 126a of the resectoscope. Handle portion 126a includes an internal knife-edge lock (not shown) that grasps bipolar electro-surgical device 104 once it has been inserted into aperture 125 of handle portion 126a. A push-button release mechanism 133 operates through an aperture 135 in handle portion 126a to release bipolar electro-surgical device 104 from the knife edge lock so that it can be removed from handle portion 126a.

Figure 17:
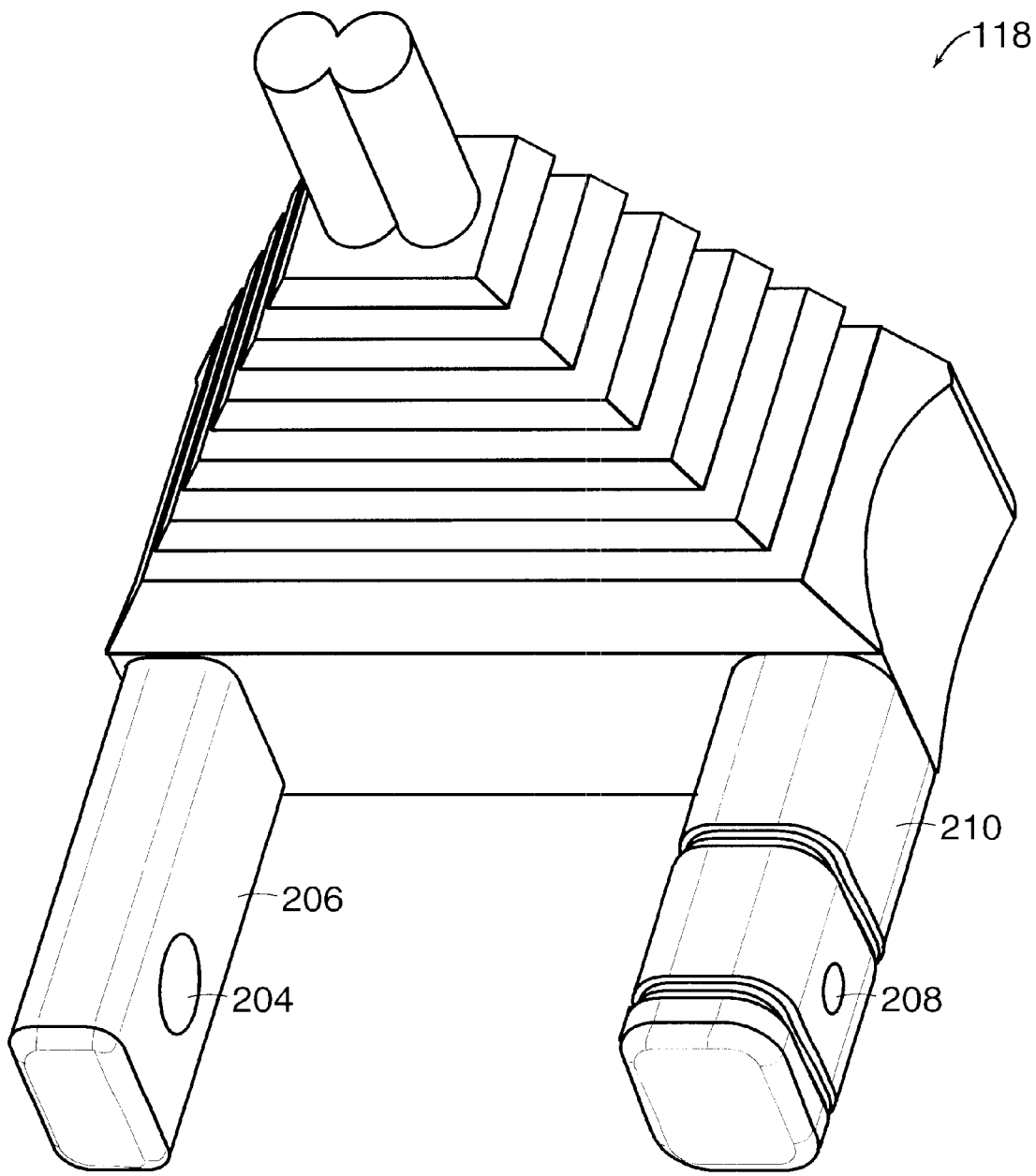
FIG. 17 is a perspective view of another bipolar power connector adaptor that can be used in conjunction with the resectoscope of FIG. 12.
Figure 18:
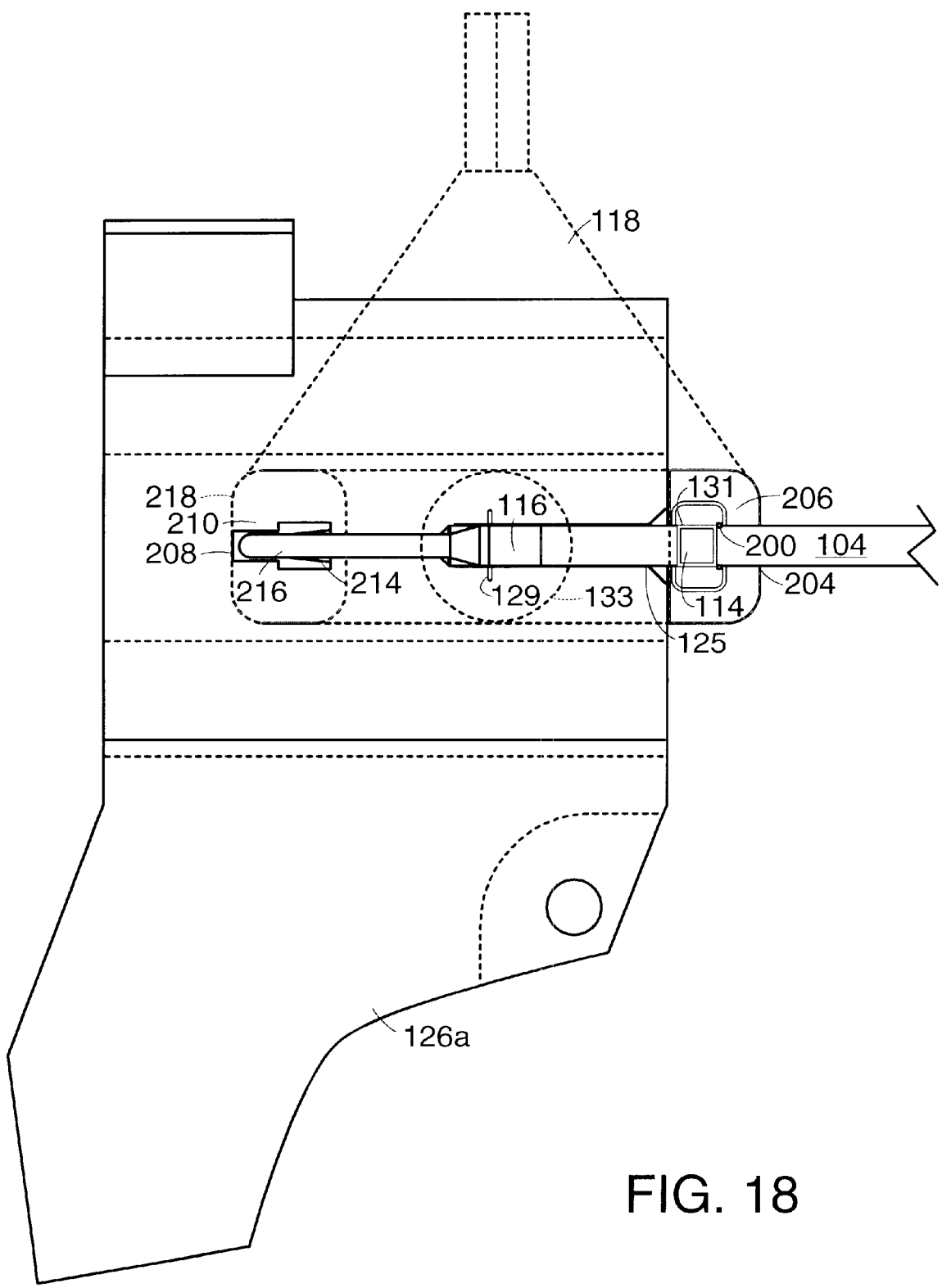
FIG. 18 is an enlarged side view of a portion of the handle of the resectoscope of FIG. 12 in combination with the bipolar power connector adaptor of FIG. 17.

FIGS. 17 and 18 illustrate one example of power connector 118 (note that the power connector shown in FIGS. 17 and 18 has a slightly different shape from the power connector shown in FIGS. 12, 13, 16, and 21a–21c). Power connector 118 (shown in dashed lines in FIG. 18) is an adaptor power connector that is attachable to an ACMI resectoscope, which is designed for use with a monopolar electro-surgical device, to allow a physician to perform bipolar electro-surgery. The adaptor power connector 118 may be an insert molded part. Arm 210 of power connector adaptor 118 fits into a hole 218 in handle portion 126a of the resectoscope. As shown, hole 218 is designed to permit an electrical connection to be made to the proximal tip of a monopolar electro-surgical device. Arm 206 of power connector adaptor 118 fits immediately adjacent to the distal edge of handle portion 126a.

Pin 116 of bipolar electro-surgical device 104 is inserted through hole 204 in arm 206 of power connector adaptor 118, into an aperture 125 in handle portion 126a of resectoscope 102, and through hole 208 in arm 210 of power connector adaptor 118. Handle portion 126a of the resectoscope includes a knife edge lock 129 for grasping a slot in pin 116. As discussed above in connection with FIG. 16, push-button release mechanism 133 in handle portion 126a releases pin 116 from knife edge lock 129 so that bipolar electro-surgical device 104 can be removed from handle portion 126a. Arm 210 of power connector adaptor 118 includes a leaf spring connector 214 for grasping bullet tip 216 of pin 116 and electrically connecting to pin 116, and arm 206 of power connector adaptor 118 includes a leaf spring connector 131 for grasping ring 114 and electrically connecting to ring 114.

An O-ring or a silicone membrane, such as, for example, a diaphragm or septum 200 is placed at the opening 202 of hole 204 in power connector adaptor 118 to prevent liquid from entering the power connector adaptor 118 and handle portion 126a and forming a conductive path between pin 116 and ring 114. Pin 116 is passed through the O-ring, diaphragm, or septum when the bipolar electro-surgical device is inserted within the power connector adaptor.

After a procedure is complete and the resectoscope 102 is removed from the patient, bipolar electro-surgical device 104 is removed from the resectoscope 102 using the push-button release and may be thrown away or cleaned. Prior to the next procedure, a physician may insert a new or cleaned electro-surgical device 104 within the resectoscope 102.

Figure 19:
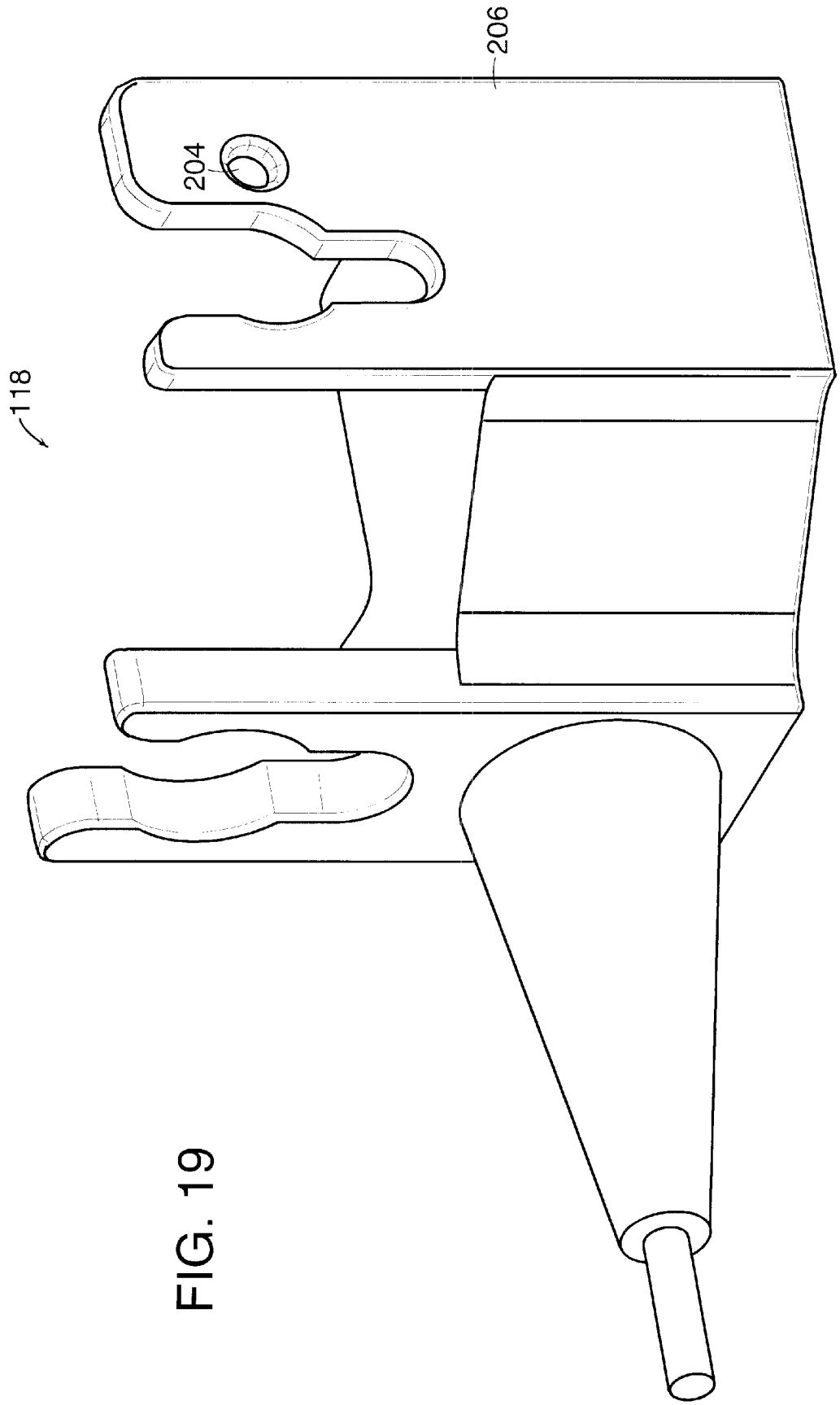
FIG. 19 is a perspective view of a power connector adaptor for use in conjunction with another type of resectoscope.
Figure 20:
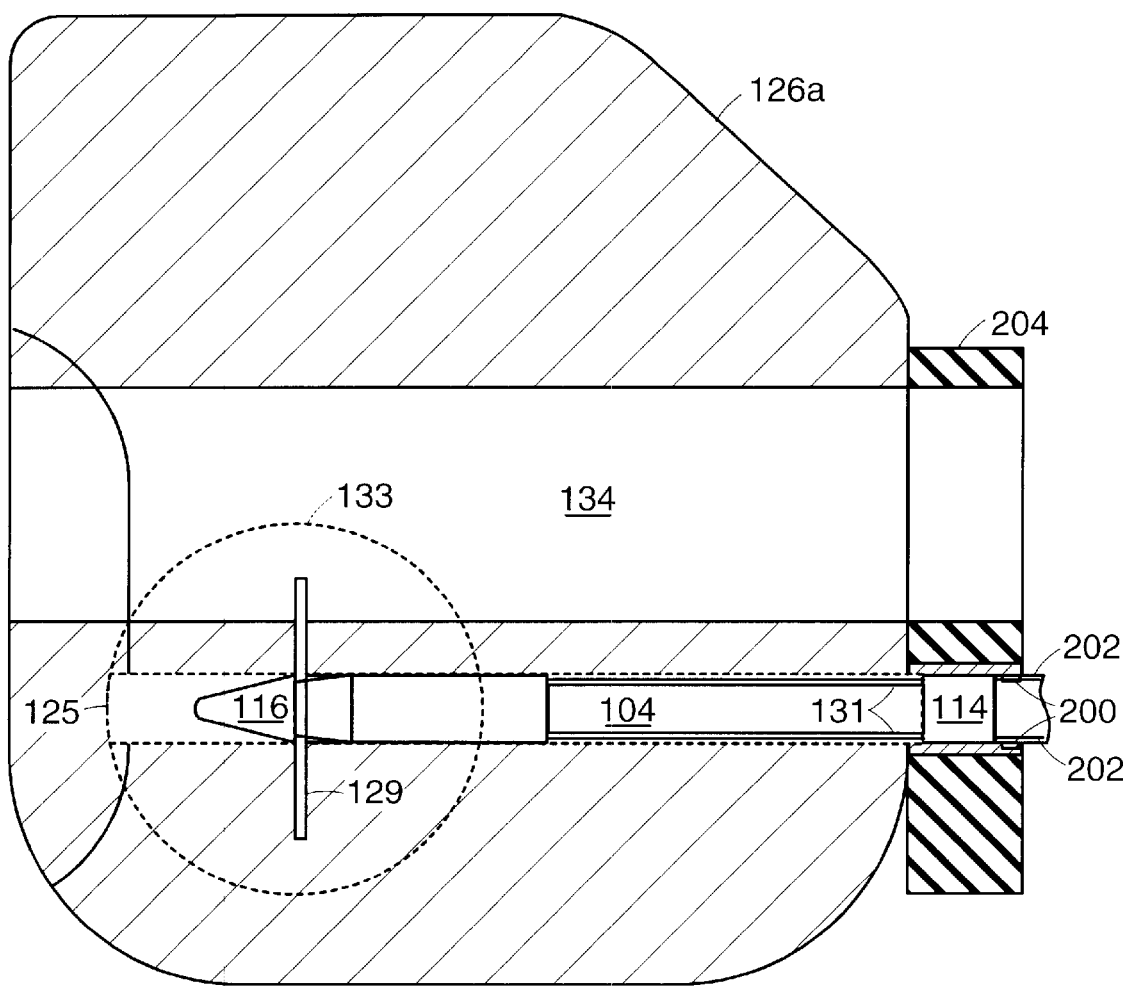
FIG. 20 is an enlarged side view, shown in partial cross-section, of the power connector adaptor of FIG. 18 and a portion of the handle of a resectoscope.

Referring to FIGS. 19 and 20, another power connector adaptor 118 is configured for use in conjunction with a Storz resectoscope rather than an ACMI resectoscope. Handle portion 126a of the Storz resectoscope includes a built-in mechanism (not shown) for electrically connecting to pin 116 of bipolar electro-surgical device 104, and power connector adaptor 118 includes a leaf spring connector 131 for grasping ring 114 and electrically connecting to ring 114. Pin 116 is inserted through 204 in arm 206 of power connector adaptor 118 and intake aperture 125 in handle portion 126a of resectoscope 102. Handle portion 126a of the resectoscope includes a push-button release mechanism 133 that operates through an aperture in handle portion 126a to release pin 116 from knife edge lock 129. An O-ring or a silicone membrane (i.e., diaphragm or septum) 200 is placed at the opening 202 of hole 204 in power connector adaptor 118 to prevent liquid from entering the power connector adaptor and handle portion 126a and forming a conductive path between pin 116 and ring 114.

Figure 21C:
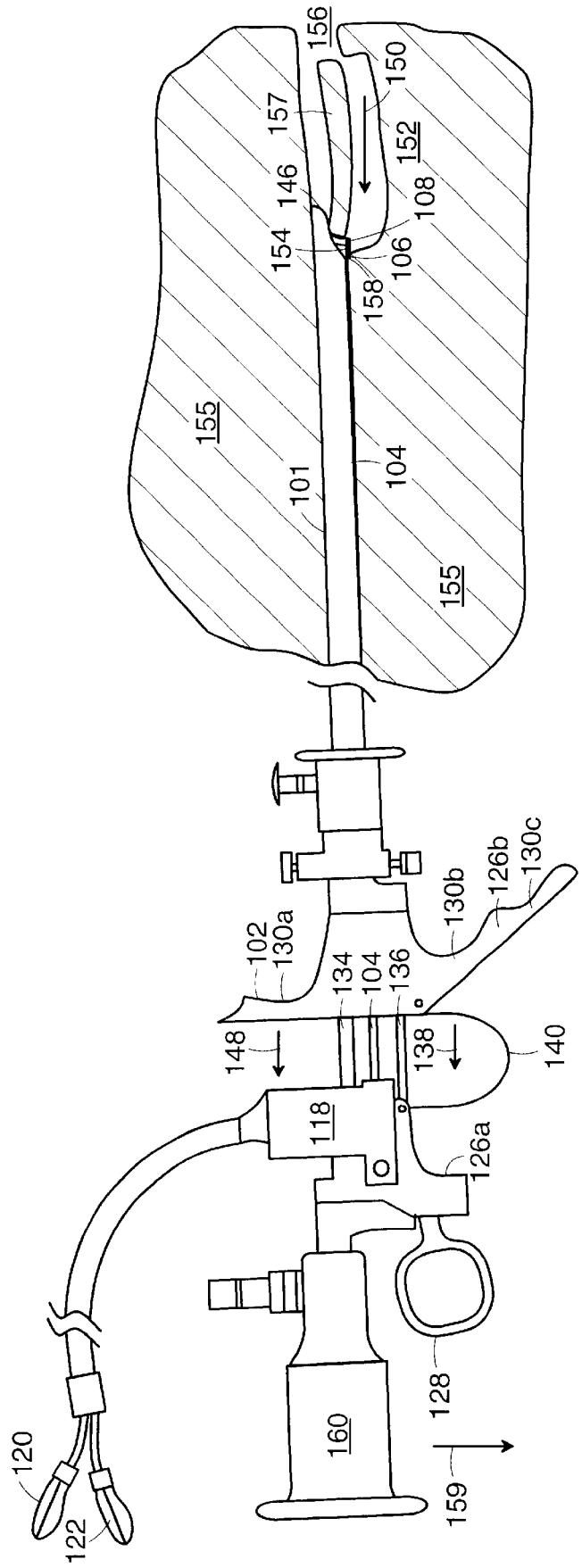

Referring to FIGS. 21a–21c, the operation of electro-surgical device 104 will be described with regard to a transurethral resectioning procedure (TURP). The patient is prepared by inserting a bullet-nosed obturator (not shown) within a sheath 101 (FIG. 13) to the region of treatment. The obturator is then removed from the sheath while leaving the sheath within the patient, and a resectoscope 102 and bipolar electro-surgical device 104 assembly is then inserted into the sheath 101. The assembly includes a telescope 160 that is inserted through rail 134 and a metal jacket 162 (FIG. 13) of resectoscope 102. With telescope 160 and irrigation, the physician inspects the region. The region is then flushed with saline.

Resectoscope 102 includes a two-piece handle having a proximal thumb piece 126a and a distal finger piece 126b. Power connector adaptor 118 is attached to thumb piece 126a. A physician inserts his thumb through ring 128 in thumb piece 126a and lays his fingers across indentations 130a, 130b, 130c in finger piece 126b and squeezes to slide (arrow 132, FIG. 21a) the thumb piece along rails 134, 136 against a force (arrow 138) provided by a spring 140. Sliding the thumb piece toward the finger piece pushes bipolar electro-surgical device 104 through metal jacket 124 in the resectoscope to cause electrodes 106, 108 to extend away from (arrow 142) distal end 123 (FIG. 13) of resectoscope 102 and a distal end 146 of sheath 101. Slide distance d6 (FIG. 21a) is equal to the distance d7 which the loop electrodes may be extended from the distal end of the sheath 101. The width W3 of the adaptor power connector is minimized to avoid decreasing the slide distance.

The physician applies power to the loop electrodes 106, 108 by turning on the RF generator and applies an upward pressure to the external end of resectoscope 102, as indicated by arrow 147, to bring the electrodes 106, 108 in contact with tissue 155. The physician then slowly releases his grip on the two-piece handle to allow the thumb piece to move away from (arrow 148, FIG. 21c) the finger piece 126b and the electrodes 106, 108 to move back toward (arrow 150) the distal end of the sheath 101. As the electrodes 106, 108 are moved back toward the sheath 101, cutting electrode 106 resects a chip 152 of tissue from a resecting path 154 within the patient's urethra 156, and current 154 passing between the electrodes 106, 108 coagulates tissue in the area 157 of the incision. When the thumb piece 126a of the handle is completely released, the electrodes 106, 108 are pulled back into the sheath and chip 152 is cut off against a lower portion 158 of the distal end of the sheath. The physician then either stops applying upward pressure to resectoscope 102 allowing urethra 156 to cause the resectoscope 102 to move in a downward direction, indicated by arrow 159, or directly applies a downward force to move the resectoscope 102 in the downward direction.

Many additional embodiments are possible. For example, the length L2 of coagulating electrode 14 (FIG. 2) can be cut with grooves (not shown) to increase the traction coagulating electrode 14 has with the tissue surface. Similarly, the surface of coagulating electrode 14 can be polished to prevent debris from sticking to coagulating electrode 14. Instead of using a roller electrode for coagulation, a sled electrode (i.e., does not roll, not shown) with the same surface area could be used. Coagulating electrode 14 is preferred, however, because as coagulating electrode 14 rolls (i.e., turns in direction 50) it prevents the build up of debris along resecting path 24. In yet another embodiment, instead of using a roller electrode for coagulation, a resilient coil wire with substantial "give" and with the same surface area could be used.

In other embodiments, a fluid flow directly over the electrodes may be provided to wash away char that could interfere with current flow. The flow could be provided by, for example, a small tube running through metal jacket 20 that terminates in a nozzle-form directed onto the electrode surfaces. In another example, the electrode and electrode lead could be hollow allowing fluid to flow and the working surface perforated such that fluid weeps from the electrode to wash away char. The fluid may be saline or another conductive fluid that does not inhibit current flow. Washing fluid flow can be initiated and terminated by a foot pedal, which may be the same foot pedal that turns on power.

Referring to FIGS. 10 and 11, to avoid leaving excess coagulated tissue region 58 in place at the end of a cut, electrodes 12 and 14 can be configured to move in an axial direction, that is, along resection path 24 independent of each other. This axial action can be achieved by passing the insulated leads to the resecting and coagulation electrodes 12, 14 through separate lumens within sheath 20. When the physician reaches the end of resection path 24, the physician uses a mechanism to independently push coagulating electrode 14 back along resecting path 24 in an axial direction, indicated by arrow 60, until coagulating electrode 14 is on an opposite side of resecting electrode 12. As a result, coagulated tissue region 58 is removed as part of chip 52. In order to move coagulating electrode 14 to an opposite side of resecting electrode 12, the width W2 (FIG. 2) of coagulating electrode 14 fork 46 is much smaller than the width W1 of resecting electrode 12 fork 48. Additionally, to prevent the two electrodes 12, 14 from coming in contact with each other, the length L2 of coagulating electrode 14 is made less than the length L1 of resecting electrode 12.

Allowing electrodes 12 and 14 to move in an axial direction independent of each other can also be used to change the direction of resection. Urging coagulating electrode 14 to an opposite side of resecting electrode 12 allows for coagulation and resection along a resecting path in a direction opposite to resecting path 24. Because a physician normally carves out several chips out of the urethra in transurethral procedure, by changing the direction of the resecting path, the physician carves a chip out with each push and then with each pull of the device.

The electrodes 12, 14 may also include a flushing apparatus to remove char. A tube 70, extending from outside the device, terminates in a nozzle 72 that directs a flow of saline onto the roller. The resecting electrode is a hollow-form with perforations 74 through which saline can be delivered to the working surface.

Coupling and pivoting mechanisms, other than the fork 46, 48 arrangement, can be employed. The maximum depth of resection may not be limited by a stop engagement. The resecting electrode 12 can be constructed such that the coagulation electrode 14 can pass beyond the mounting for the resecting electrode 12. If the width of the fork of the coagulating electrode 14 is less than the width between the two loop halves of the resecting electrode 12, the depth of resection is not limited. Using the telescope 30, the physician can manually control the maximum depth of resection. Coagulation may be carried out just after resection, by reversing the orientation of the electrodes.

The electro-surgical devices can be constructed for use in various procedures, including endoscopic, laparoscopic (i.e., the electrode configuration extends through a trocar), and cystoscopic procedures. The device can have a flexible shaft for delivery deep into the body. The devices can be configured for removal or debuiking of tumors in, e.g., the esophagus, cervix, or uterus (myomectomy), or for removal of liver lobe sections or removal of any protruding vascular tissue. The devices may also be configured to resect the lining of the uterus (endometrioma) or for use in transurethral resectioning of the bladder (TURB).

The devices can be constructed to carry multiple different resecting and/or coagulating electrodes among which power can be switched to vary the depth or width of treatment. For example, the device may carry two resecting loops arranged and of different size to allow cutting to different maximum depths. Differently shaped coagulating electrodes can be carried to vary the coagulation pattern. By switching among the different electrodes, the physician can tailor the treatment without removing the device from the body. The different electrodes can be arranged in parallel about or in series along the device axis. The power applied to the device can be varied with device construction and purpose (tissue type). Small scale devices, e.g., for use in the brain, may use lower power settings, e.g., 10 Watts. The arrangement can be adapted for a hand-held device for use in open surgery. Moreover, the resecting electrode can be replaced with a different shaped small surface area resecting electrode, and the coagulating electrode can be replaced with a different shaped larger surface area coagulating electrode.

With reference to FIG. 22, there is shown a modified version of bipolar electro-surgical device 104 shown in FIG. 13 In the modified bipolar electro-surgical device 104, the device 104 includes a loop electrode 106 but instead of providing a coagulating electrode (electrode 108 in FIG. 13), insulator jacket 112 is constructed to allow a steady stream of saline solution to be injected into the area to be coagulated. Current 107 passes between the electrode 106 and the saline stream. Insulator jacket 112 is constructed so as to maintain the saline solution in electrical contact with ring 114 or pin 116 at the proximal end of the bipolar electro-surgical device 104. The steady stream of saline solution functions as the equivalent of a thin, small diameter wire and coagulates tissue in a manner similar to, and with the same effect as, the embodiment of FIG. 13. However, the embodiment of FIG. 22 has the advantage that the initial impedance across the output leads of the RF generator can be higher than the initial impedance in the embodiment of FIG. 13. This is important because certain RF generators are constructed, for safety reasons, to assume that if the initial impedance across the output leads is relatively low, a short circuit might be present. Under such conditions, the output current starts out low and then builds up as the RF generator learns that there is in fact no short circuit. The embodiment of FIG. 22, in contrast can avoid this current build-up time.

With reference to FIGS. 23–25, there is shown another bipolar electro-surgical device, having wedge-like resecting electrode 222 and loop return electrode 224 positioned at the ends of insulated wires 228 and 230. The bipolar electro-surgical device is positioned within an electrically conductive environment such as a saline field 232 that is injected through resectoscope sheath 226. When the bipolar electro-surgical device is extended as shown in FIG. 24 and resecting electrode 222 is placed in contact with tissue, current passes from the resecting electrode 222 through the, tissue and through saline 232 to return electrode 224, if the resectoscope sheath 226 is nonconductive. If the resectoscope sheath 226 is conductive, current passes from resecting electrode 222 through the tissue to resectoscope sheath 226, and then from the resectoscope sheath 226 through saline 232 to return electrode 224. An alternative embodiment is shown in FIG. 26, in which resecting electrode 222 is a wedge-like electrode as in FIGS. 23–25 but return electrode 224 is an exposed wire rather than a loop.

The present invention further contemplates the use of monopolar and bipolar electro-surgical devices for performing tissue resection. As further described, a monopolar electro-surgical device uses a single resecting electrode along with a surface return electrode. In the present invention, the monopolar electro-surgical device performs both resection and coagulation. When power is applied to the monopolar resecting electrode, current density is concentrated at the tip of the resecting electrode, and a plasma field is generated as the electrode contacts the tissue. Generation of the plasma field causes heating of the tissue sufficient to resect the tissue.

In the present invention, the electro-surgical devices can be efficiently used with liquid mediums such as water, saline, glycine, or sorbitol. In one preferred embodiment, saline, a fluid which is electrolytic, isotonic and non-osmotic can be used. As briefly described above, the use of saline with monopolar electro-surgical devices, however, poses several problems. Because saline is conductive, it is often difficult to generate a plasma field at the tip of the monopolar resecting electrode as current applied to the electrode quickly diffuses toward the saline and does not focus at the electrode tip. Moreover, an RF generator in communication with the electrode will sense that a short circuit is present at the electrode tip, because saline provides a low initial impedance across the output leads. Therefore, the output voltage starts low and then builds up as the RF generator learns that an impedance exists at the tip. The impedance builds up as the electrode is heated, causing the fluid in contact with the electrode to vaporize. The result is then an increase in the impedance of the system. The RF generator responds by increasing the amount of power delivered. This continues in the manufacturer's specified working impedance range. Above this range, the RF generator delivers decreasing amounts of power.

The electro-surgical devices of the present invention overcome these problems by being able to focus energy emission towards the tissue, preventing energy loss to the resected chips or the fluid delivered to the tissue site, while avoiding the need for higher power levels to achieve such an effect. The end effect is the increase in current density at the electrode. Moreover, the resecting electrodes of the present invention are capable of generating plasma fields in a tissue being irrigated with fluid, such as, for example, a non-osmotic fluid such as saline, glycine or sorbitol, without being embedded, within tissue. In addition, lower power levels can be used with the electro-surgical devices of the present invention in performing resection procedures, since diffusion of energy at the distal tip of the resecting electrode has been reduced.

Figure 27A:
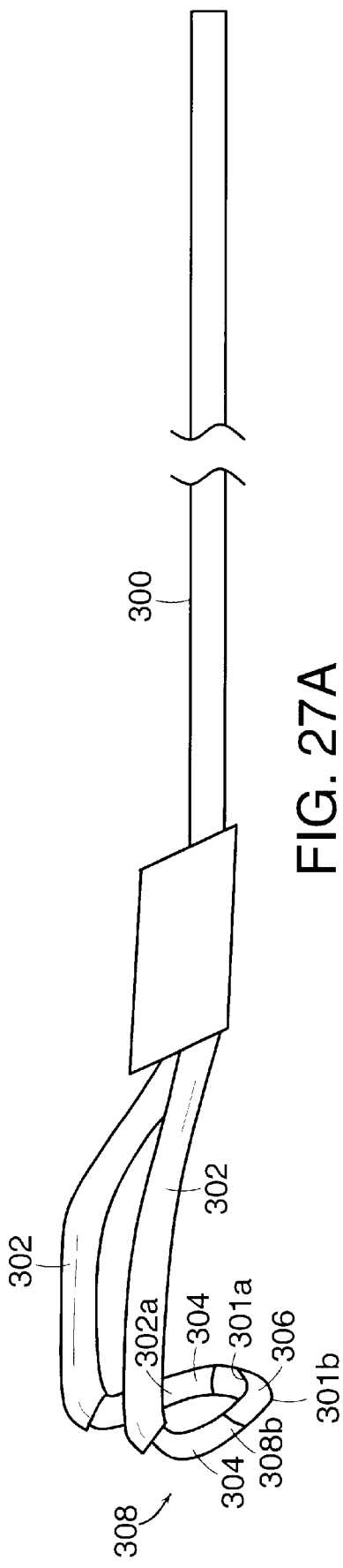
FIG. 27a is a perspective view of an electro-surgical device having a loop electrode.
Figure 27B:
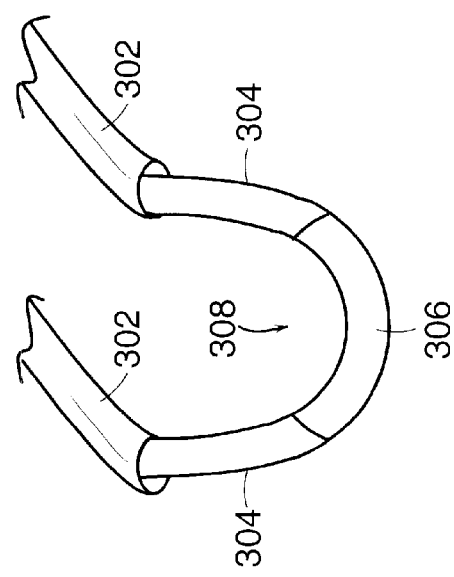

Referring to FIGS. 27a and 27b, an electro-surgical device includes an elongated body 300, a pair of arms 302 extending from a distal end of the elongated body 300, and a loop electrode 308 connecting the pair of arms 302. The proximal end of the elongated body 300 is adapted to be coupled to an energy source (not shown). Suitable conductive materials for the loop electrode 308, can include, for example, stainless steel, tungsten, titanium, aluminum, brass, silver alloy, copper alloy, as well as other materials exhibiting conductive properties. The loop electrode 308 comprises inner and outer flat surfaces 303a, 303b, and proximal and distal edges 301a, 301b. In one embodiment, the proximal edge 301a can be sharp to aid in performing resection. The loop electrode 308 defines a pair of end sections 304 and a base section 306. Each end section 304 is coupled to an arm 302 and can comprise the conductive material having an insulative coating or sheath disposed thereon as further described. The base section 306 lies between the end sections 304 and, in the present embodiment comprises the conductive material without an insulative coating. The base section 306 is the first region to be contacting the target tissue. The electro-surgical device can further include a sheath or tubular member enclosing the elongated body 300 and for delivering fluid such as saline, glycine or sorbitol to a treatment path. In this embodiment, energy applied to the electrode 308 remains focused at the base section 306 when the probe is used along with an electrolytic fluid such as, for example, saline.

In the present embodiment, the insulative coating disposed on the end sections 304 comprises a material capable of remaining adhered to the conductive material forming the loop electrode 308, upon application of a voltage of up to about 1000 volts to 2000 volts and upon generation of a plasma field near the electrode 308. The pair of arms 302 can be surrounded by an insulation sheath, or, in an alternative embodiment, the pair of arms 302 can have the same insulative coating covering the end sections 304 in addition to or instead of the insulation sheath. It is to be appreciated that finding the appropriate insulator for the coating is not a trivial matter as most insulators can disintegrate upon generation of plasma fields. A preferred insulator used in the present embodiment can have superior electrical resistivity, dielectric strength, and hardness, in addition to having good adhesion to the conductive material forming the loop electrode 308.

In a preferred embodiment, the insulative coating disposed on the end sections 304 can be a diamond-like carbon (DLC) coating sold under the trademark Diamonex® by Diamonex, a unit of Monsanto Company (Allentown, Pa.). DLC is an amorphous diamond material which resembles properties of a naturally occurring diamond. DLC has a hardness in the range from 1000 to 5000 kg/mm$^2$, an electrical resistivity in the range from $10^4$ to $10^{12}$ ohms-cm, a dielectric constant of approximately 100 volts (rms) at mains frequency and good adhesion to a substrate.

In an alternative embodiment, synthetic polycrystalline diamond can be used as insulative coating on the end sections 304. Polycrystalline diamond has a thermal conductivity greater than 1000 W/m° K, an electrical resistivity of greater than $10^{11}$ ohm-cm, a thermal expansion of about $2 \times 10^{-6}$/° C. between 25° C. and 200° C., a dielectric constant of about 5.7, a dielectric strength of about 300+V/$\mu$m, and a shear strength of about $10^8$N/m$^2$.

In one embodiment, DLC is vapor deposited onto the loop electrode 308. In other embodiments, the DLC can be deposited by ion beam deposition, RF plasma deposition and by the process of polycrystalline growth. As will be further described, vapor deposition is a microfabrication technology well known to those skilled in the electronics fabrication art. Ion beam deposition technique is described in U.S. Pat. No. 5,508,368, which is incorporated herein by reference. In another embodiment, DLC is deposited using a hot filament chemical vapor deposition technique. The DLC coating on the base section 306 is then removed by etching or other removal processes, such as grinding and EDM (Electrical Discharge Machining) while the DLC coating on the end sections 304 remains. In another embodiment, the base section 306 is masked while DLC is vapor deposited on the loop electrode 308, such that DLC is prevented from depositing on the base section 306.

Figure 28:
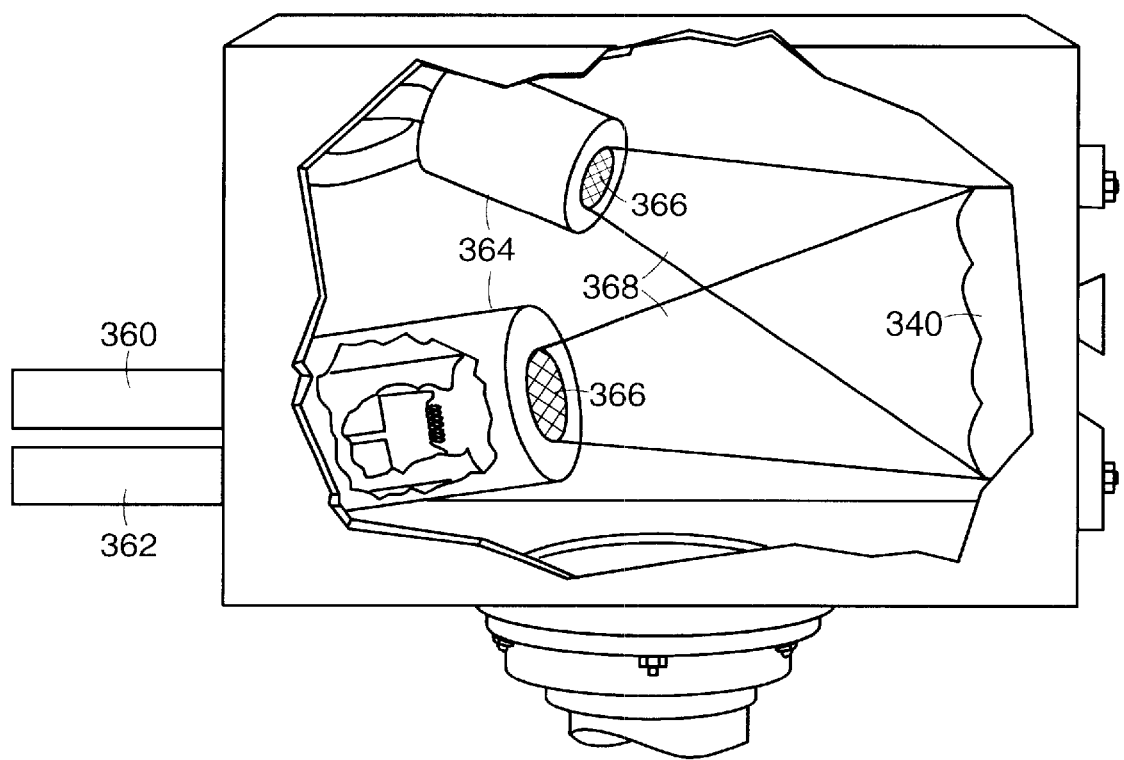
FIG. 28 is a cross-sectional view of a dual ion beam deposition chamber for depositing an insulative coating on an electrode.

As shown in FIG. 28, in a dual ion beam deposition process, plasma is generated by applying a mixture of hydrocarbon and argon gases 360, 362 to each ion source 364. Electrically charged grids 366 are placed at one end of the ion source 364. The grids 366 extract and accelerate the hydrocarbon and argon ions 368 toward a substrate 370 to be coated. The substrate 370 is maintained at a temperature between 20° C. and 50° C. as the substrate 370 is sufficiently remote from the plasma within the ion source 364. The accelerated ions 368 combine on the surface of the substrate 370 to produce an amorphous carbon coating. The process causes some of the ions to embed in the substrate 370 thereby providing excellent adhesion. The DLC coating placed on the end sections 304 can have a thickness up to about 10 microns. It is to be appreciated that this thickness can vary depending on the intended application of the device. For example, in one embodiment, the film is evenly deposited and the thickness of the film can vary from about 6 microns to about 10 microns.

Referring to FIGS. 29a and 29b, the electro-surgical device 310 includes an elongated body 312, a pair of arms 314 extending from a distal end of the elongated body 312, and an electrode 316 in communication with the pair of arms 314. The electrode 316 has a plurality of randomly dispersed conductive regions 318. The conductive regions 318 are created by a non-uniformly deposited insulative coating 320 on the electrode 316. Such non-uniform deposition allows energy emission to preferentially breakthrough the thinner coated regions. In this embodiment, the thickness of the film can be as small as 1 micron, for example and as large as, for example, about 10 microns. It is to be appreciated however, that the thickness of the film in other embodiment's can be greater than 10 microns or less than 1 micron. Although the conductive regions 318 are dispersed, the conductive regions 318 are capable of transmitting a current of up to 2 Amps to tissue disposed near the conductive regions 318 in order to perform resection. It is to be appreciated that higher currents can be supplied depending on the intended application.

In another embodiment, the conductive regions 318 can comprise a plurality of pin holes created by the process of vapor deposition of the insulative coating 320 on the electrode, described above. The electro-surgical device can further include a sheath for carrying the elongated body 312 and for delivering an electrolytic non-osmotic fluid such as saline, to a treatment path. In this embodiment, energy applied to the electrode 316 remains focused at the conductive regions 318 when used in conjunction with an electrolytic fluid.

As shown in the embodiment of FIGS. 29a and 29b, the electrode 316 comprises a substantially U-shaped loop electrode. The insulative coating, however, may be placed on other types of electrodes such as a cylindrical roller electrode or a spherical roller electrode, as shown in FIGS. 30a and 30b, respectively.

Referring to the embodiment of FIG. 30a, the electro-surgical device includes an elongated body 321, a pair of arms 323 in communication with the distal end of the elongated body 321, and a cylindrical roller electrode 322 connected to the pair of arms 323. The arms 323 can have an insulative sheath 324 or coating disposed thereon, and the roller electrode 322 can be completely or partially conductive. For example, only the outer portions 325a of the roller electrode 322 can be coated with a DLC or other coating having a certain resistance to cracking at high temperatures and high voltages. In this regard, energy is focused in the middle of the roller electrode 325b. Alternatively, the roller electrode 327 can include an uneven deposition of insulative coating such as that shown in FIG. 30b.

Referring to the embodiment of FIG. 30b, an electro-surgical device includes an elongated body 328 in communication with a pair of arms 326 at a distal end, and a spherical roller ball electrode 327 connecting the pair of arms 326. The spherical rollerball electrode 327 operates in a similar fashion as described in the embodiment of FIGS. 29a and 29b. The uneven deposition of a DLC or other coating 329b allows energy to be focused at the conductive regions 329a of the roller ball electrode 327. It is to be appreciated that the embodiments described in FIG. 30a and FIG. 30b can further include a sheath enclosing the elongated body 321, 328 for delivering fluid to the treatment site.

Figure 31A:
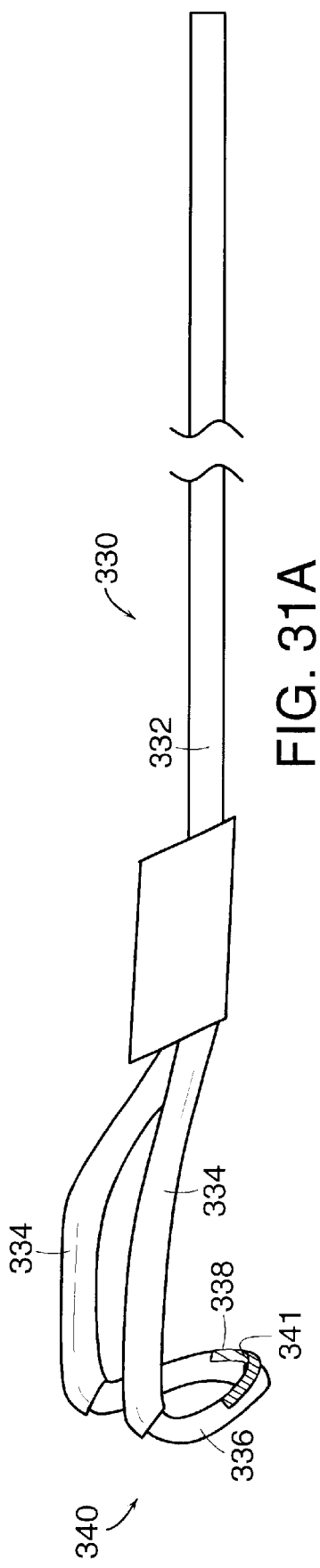
FIG. 31a is a perspective view of another electro-surgical device having a loop electrode.
Figure 31B:
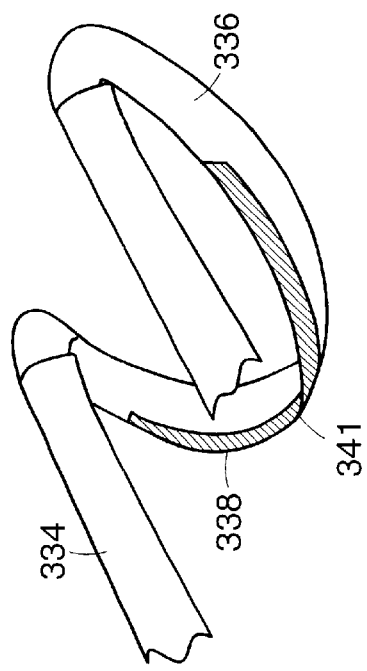

Referring to FIGS. 31a and 31b, the electro-surgical device 330 includes an elongated body 332, a pair of arms 334 extending from a distal end of the elongated body 332, and an electrode 340 in communication with the pair of arms 334. The pair of arms 334 can have an insulative sheath or coating, as described above. In this embodiment, the electrode 340 has a first region 336 covered with an insulative coating and a second region 338 covered with graphite. By coating the second region 338 with graphite, the second region 338 is masked while the first region is subsequently coated with the insulative coating, such as DLC or other insulative material. Graphite is placed on the second region 338 by dipping, brushing, and spraying. The graphite covering does not allow the insulator to bond to it, and thus leaves the second region 338 free of insulative coating. The graphite that remains on the second region 338 thereafter disintegrates upon the application of a voltage of greater than 100 volts (peak to peak) at RF frequency to the electrode 340 and exposes a conductive region underneath. Thus the conductive region is exposed and energy is focused at the conductive region during a resection procedure.

As shown in the embodiment of FIGS. 31a and 31b, the electrode 340 is a loop electrode having a sharp proximal edge 341 used in resection. The second region 338 comprises an area immediately adjacent the sharp proximal edge 341, and the first region 336 comprises the remainder of the electrode 340. The electro-surgical device 330 can further include a sheath for carrying the elongated body 332 and for delivering a non-osmotic fluid such as saline, glycine or sorbitol to a treatment path. In this embodiment, energy applied to the electrode 340 remains focused at the second region 318 when used in conjunction with a fluid.

Figure 32:
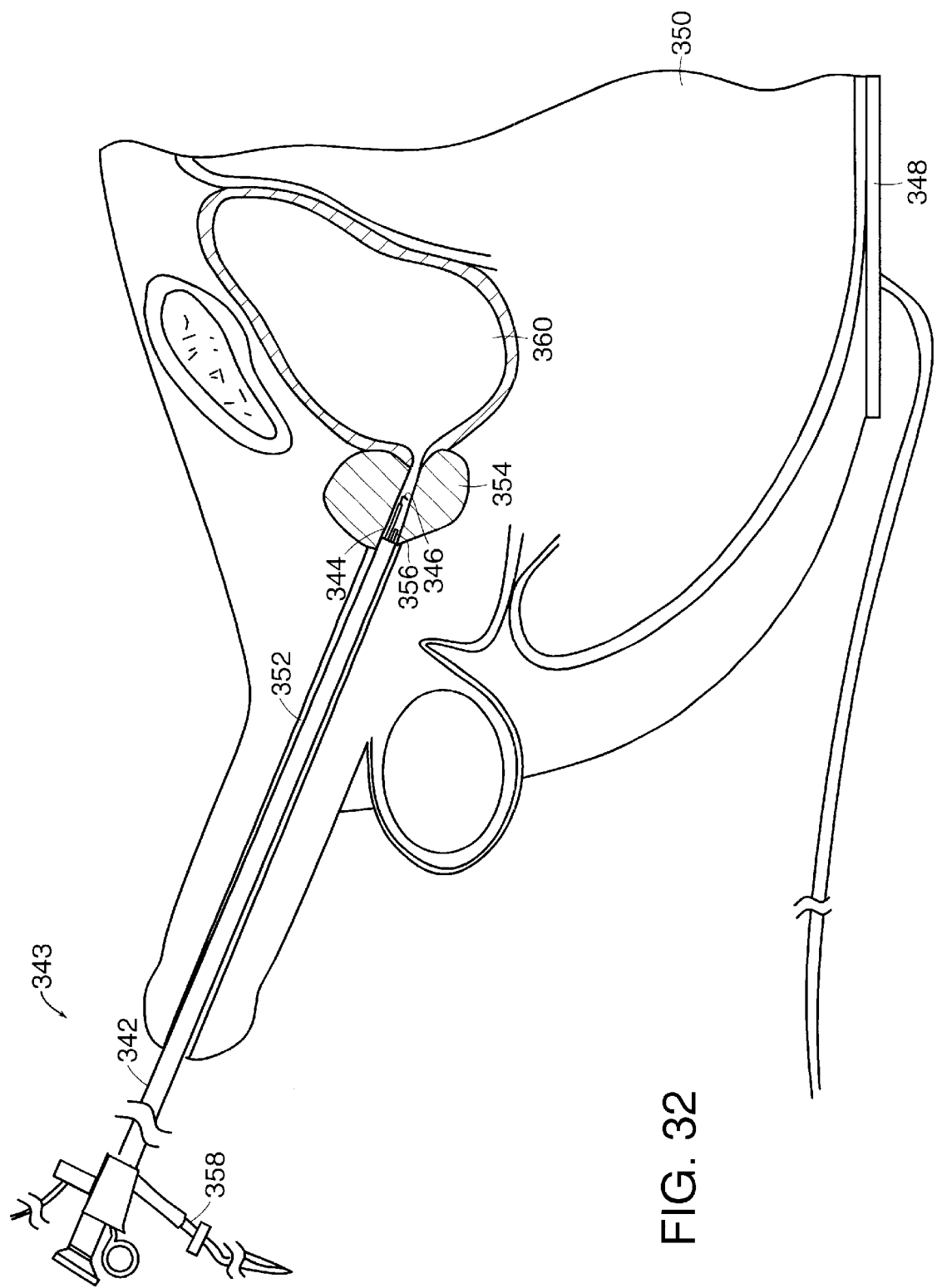
FIG. 32 is a side view illustrating selective resection and cauterization of prostate tissue using the electro-surgical device of the present invention.
Figure 33A:
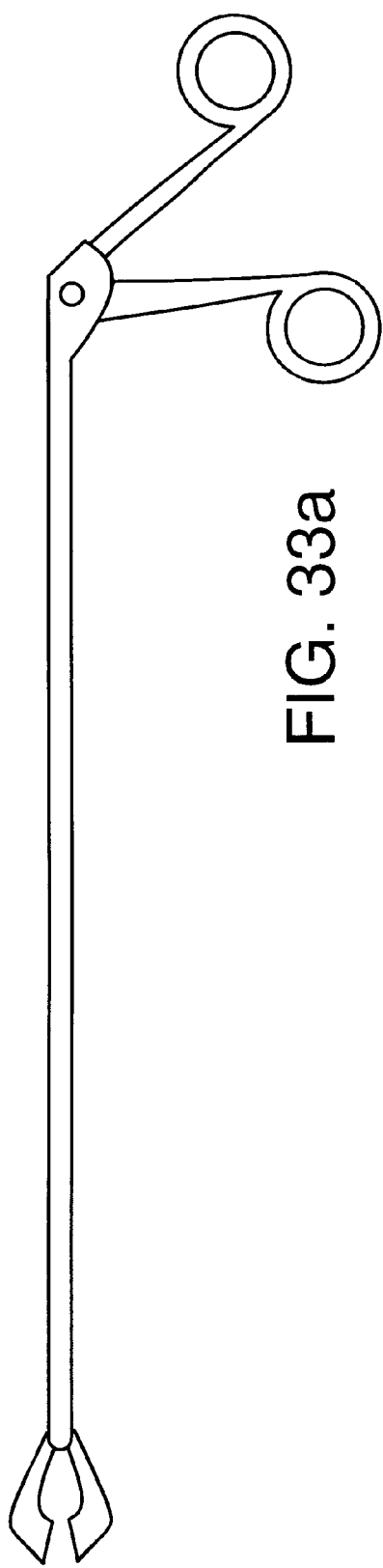
FIG. 33a is a side view of a biopsy forcep—.
Figure 33B:
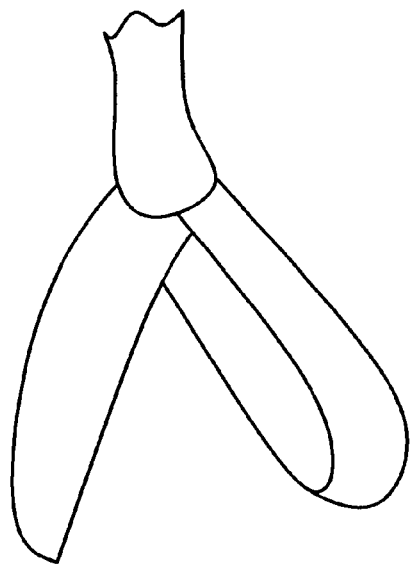

Referring to FIG. 32, a resectoscope assembly 343 includes a resectoscope 342 defining a channel (not shown) and an electro-surgical device 344 insertable through the channel. The electro-surgical device 344 may be of any embodiment described above with reference to FIGS. 27a to 30b. As illustrated in FIG. 32, in a typical transurethral procedure, a return electrode 348 is positioned on a surface of the body 350 and the resectoscope assembly 342 is inserted inside the urethra 352. The electro-surgical device 344 is inserted through the channel of the resectoscope 342 and positioned along a treatment path near prostate tissue 354 to be resected. The resectoscope 342 includes a telescope 356 at a distal end, such that the electro-surgical device 344 can be positioned under observation. The tissue to be resected is flushed with a non-osmotic fluid introduced through a luer port 358 for injecting fluid. In a preferred embodiment, the non-osmotic fluid can be a non-osmotic, electrolytic fluid such as saline. Alternatively, the non-osmotic fluid can be a non-osmotic, non-electrolytic fluid such as glycine or sorbitol. A voltage in the range from about 1000 volts to 2000 volts (peak to peak) is applied across the resecting electrode 346 and the return electrode 348 to generate a plasma field, without embedding the resecting electrode 346 inside the prostate tissue 354. The resecting electrode 346 is moved along the treatment path to resect and coagulate the prostate tissue 354.

Although a resection procedure using the resecting electrode of the present invention have been described with reference to FIG. 32, resection of tissues other than prostate tissues can be performed according to the invention. For example, the resectoscope assembly 343 can be inserted deeper into the bladder 360 to resect bladder tissues. Alternatively, the resectoscope assembly 343 can be inserted inside a female patient to resect a tumor from the walls of the uterus or to resect an endometrium lining. In addition, bipolar electrodes in addition to monopolar electrodes can be selectively coated with an insulative coating for limiting current distribution according to the invention.

It is to be appreciated that the use of a DLC coating can have other applications. For example, biopsy forceps can be selectively coated with an insulative coating to prevent the biopsy sample from being damaged. The inner surfaces of the biopsy forcep that comes in contact with the removed biopsy sample can be coated with the insulative coating, while the outer surfaces of the forceps used to remove the sample can remain conductive.

There have been described novel and improved apparatus and techniques for electro-surgical tissue removal. It is evident that those skilled in the art may now make numerous uses and modifications of and departures from the embodiments described herein without departing from the invention. Consequently, other embodiments are within the following claims.

What is claimed is:

1. An electro-surgical device for tissue resection, comprising:

an elongated body adapted to be coupled to a source of energy at a proximal end;

a substantially U-shaped loop electrode;

a pair of arms comprising a long axis, the pair of arms in a spaced relationship extending from a distal end of the elongated body to the loop electrode and defining a plane, the pair of arms surrounded by a first insulative coating along the long axis of each arm, the first insulative coating extending from the elongated body to the loop electrode, wherein the substantially U-shaped loop electrode connects the pair of arms at an angle relative to the plane, the loop electrode defining a pair of end sections and a base section, each end section coupled to an arm, the end sections comprising a conductive material and including a second insulative coating disposed thereon, the base section consisting of a continuous curve disposed between the end sections and comprising the conductive material free of the first and second insulative coatings, wherein energy applied to the electrode focuses energy emission for tissue resection at the continuously curved base section.

2. The electro-surgical device of claim 1, wherein the insulative coating is capable of remaining adhered to the end sections upon application of a voltage of up to from about 1000 volts to about 2000 volts peak to peak at RF frequency to the electrode.

3. The electro-surgical device of claim 1, wherein the insulative coating comprises a diamond-like carbon coating.

4. The electro-surgical device of claim 1, wherein the insulative coating comprises a material that remains adhered to the pair of arms while a plasma field flows through the electrode.

5. The electro-surgical device of claim 1, wherein the insulative coating is vapor deposited onto the end sections according to one of the following procedures: vapor deposition, ion deposition, RF deposition, or polycrystalline growth.

6. The electro-surgical device of claim 1, wherein the insulative coating comprises a vapor deposited coating.

7. The electro-surgical device of claim 1, wherein the insulative coating has a thickness of up to about 10 microns.

8. The electro-surgical device of claim 1, wherein the base section has a proximal sharp edge.

9. The electro-surgical device of claim 1, wherein the loop defines an acute angle with the pair of arms.

10. The electro-surgical device of claim 1, further comprising a sheath enclosing the elongated body, the sheath for delivering a non-osmotic fluid to a treatment path.

11. The electro-surgical device of claim 1, further comprising a sheath enclosing the elongated body, the sheath for delivering saline to a treatment path.

12. The electro-surgical device of claim 1, further comprising a sheath for enclosing the elongated body, the sheath for delivering glycine to a treatment path.

* * * * *

UNITED STATES PATENT AND TRADEMARK OFFICE
CERTIFICATE OF CORRECTION

PATENT NO. : 6,494,881 B1
DATED : December 17, 2002
INVENTOR(S) : Thomas O. Bales et al.

It is certified that error appears in the above-identified patent and that said Letters Patent is hereby corrected as shown below:

Title page, Item [54] and Column 1, line 2,
Title, please replace "ELECTRODE-SURGICAL" with -- ELECTRO-SURGICAL --;

Title page,
Item [56], References Cited, FOREIGN PATENT DOCUMENT, please insert
-- DE 2514501      10/1976
   WO 93/21845     11/1993 --.
U.S. PATENT DOCUMENTS, please insert
-- 5,354,295 A    10/1994    Guglielmi et al.
   5,354,296      10/1994    Turkel
   5,376,087      12/1994    Haber et al.
   5,397,342      03/1995    Heil, Jr. et al.
   5,478,350      12/1995    Kratsch et al.
   5,482,037      01/1996    Borghi
   5,549,605      08/1996    Hahnen
   5,603,711      02/1997    Parins et al. --.
OTHER PUBLICATIONS," please insert -- http://members.aol.com/getscc, 10/26/98, 6 pages --.

Signed and Sealed this

Sixth Day of July, 2004

JON W. DUDAS
*Acting Director of the United States Patent and Trademark Office*